US012642753B2

(12) United States Patent
Richard et al.

(10) Patent No.: US 12,642,753 B2
(45) Date of Patent: Jun. 2, 2026

(54) DENTAL HYDRAULIC CEMENT COMPRISING ULTRAFINE CALCIUM SILICATE PARTICLES HAVING FAST HARDENING AND SUITABLE MECHANICAL PROPERTIES

(71) Applicant: SEPTODONT OU SEPTODONT SAS OU SPECIALITES SEPTODONT, Saint-Maurdes Fossés (FR)

(72) Inventors: Gilles Richard, Saint-Maur-des-Fossés (FR); Olivier Marie, Saint-Maur-des-Fossés (FR); Clémence Co, Saint-Maur-des-Fossés (FR)

(73) Assignee: SEPTODONT OU SEPTODONT SAS OU SPECIALITES SEPTQDONT, Saint-Maur-des-Fossés (FR)

( * ) Notice: Subject to any disclaimer, the term of this patent is extended or adjusted under 35 U.S.C. 154(b) by 807 days.

(21) Appl. No.: 17/625,830

(22) PCT Filed: Jul. 17, 2020

(86) PCT No.: PCT/EP2020/070350
§ 371 (c)(1),
(2) Date: Jan. 10, 2022

(87) PCT Pub. No.: WO2021/009369
PCT Pub. Date: Jan. 21, 2021

(65) Prior Publication Data
US 2022/0265518 A1     Aug. 25, 2022

(30) Foreign Application Priority Data
Jul. 18, 2019     (EP) ..................................... 19305951

(51) Int. Cl.
| | |
|---|---|
| A61K 6/76 | (2020.01) |
| A61K 6/71 | (2020.01) |
| A61K 6/818 | (2020.01) |
| A61K 6/822 | (2020.01) |
| A61K 6/851 | (2020.01) |
| A61K 6/853 | (2020.01) |
| A61K 6/876 | (2020.01) |
| C04B 14/04 | (2006.01) |
| C04B 111/00 | (2006.01) |

(52) U.S. Cl.
CPC .................. *A61K 6/76* (2020.01); *A61K 6/71* (2020.01); *A61K 6/818* (2020.01); *A61K 6/822* (2020.01); *A61K 6/851* (2020.01); *A61K 6/853* (2020.01); *A61K 6/876* (2020.01); *C04B 14/043* (2013.01); *C04B 2111/00836* (2013.01)

(58) Field of Classification Search
None
See application file for complete search history.

(56) References Cited

U.S. PATENT DOCUMENTS

| | | | |
|---|---|---|---|
| 7,553,362 B2 | 6/2009 | Lu et al. | |
| 7,819,663 B2 | 10/2010 | Bergaya et al. | |
| 8,722,100 B2 | 5/2014 | Lovschall et al. | |
| 8,974,586 B2 | 3/2015 | Richard et al. | |
| 9,427,380 B2 | 8/2016 | Richard et al. | |
| 2006/0102049 A1 | 5/2006 | Bergaya et al. | |
| 2010/0291512 A1 | 11/2010 | Yoo et al. | |
| 2014/0124573 A1 | 5/2014 | Doi et al. | |
| 2014/0134573 A1 | 5/2014 | Torabinejad et al. | |
| 2014/0224151 A1* | 8/2014 | Richard | A61K 6/60 106/35 |
| 2016/0128911 A1 | 5/2016 | Fontein et al. | |
| 2018/0214247 A1* | 8/2018 | Sharma | A61C 5/50 |
| 2020/0085847 A1* | 3/2020 | Bellinati | C04B 28/14 |

FOREIGN PATENT DOCUMENTS

| | | |
|---|---|---|
| CN | 102947244 A | 2/2013 |
| EP | 2558431 B1 | 6/2020 |
| WO | 2015119954 A1 | 8/2012 |

OTHER PUBLICATIONS

Belio-Reyes et al. (Journal of Endoscopics vol. 35 (6) 2009 875-878). (Year: 2009).*
European Search Report mailed Sep. 25, 2020, in International Application No. PCT/EP2020/070358; 4 pages.
Mohammad Reza Sanaee et al., "The influence of particle size and multi-walled carbon nanotube on physical properties of mineral trioxide aggregate", Material Research Express, 2019, vol. 6; No. 6, 065413; 20 pages.
William N. Ha et al., "D90: The Strongest Contributor to Setting Time in Mineral Trioxide Aggregate and Portland Cement"; Basic Research Technology; Journal o Endodontics; American Association of Endodontist 2015; vol. 41; No. 7; Jul. 1, 2015; XP055659903; pp. 1146-1150.
Saeed Asgary et al. "Comparison of Mineral Trioxide Aggregate's Composition with Portland Cements and a New Endodontic Cement"; Journal of Endodontic; Basic Research Technology; vol. 35; No. 2; Feb. 1, 2009; KP02588072; pp. 243-250.
B.W. Darvell et al., "MTA"—An Hydraulic Silicate Cement: Review update and setting reaction; Dental Materials, Elsevier; vol. 27; No. 5; Feb. 3, 2011; XP028158967; pp. 407-422.

* cited by examiner

*Primary Examiner* — Robert T Butcher
(74) *Attorney, Agent, or Firm* — Maier & Maier, PLLC

(57) ABSTRACT

A dental restoration material made from a dental hydraulic cement that includes ultrafine calcium silicate (UCS) particles, in the presence of a limited amount of water, so that the hydraulic cement fast hardens while providing a material having suitable mechanical properties for dental restoration, and especially a high compressive strength.

20 Claims, 2 Drawing Sheets

DENTAL HYDRAULIC CEMENT COMPRISING ULTRAFINE CALCIUM SILICATE PARTICLES HAVING FAST HARDENING AND SUITABLE MECHANICAL PROPERTIES

FIELD

The present invention relates to the field of dentistry. Especially, the invention relates to the provision of a dental restoration material, from a dental hydraulic cement comprising ultrafine calcium silicate (UCS) particles, obtained in presence of a limited amount of water, so that the hydraulic cement fast hardens while providing a material having suitable mechanical properties for dental restoration, and especially a high compressive strength.

The UCS particles used in the dental hydraulic cement of the invention have finely tuned $d_{10}$, $d_{50}$ and $d_{90}$ sizes, and specific area.

BACKGROUND

Dental restoration aims at restoring of the integrity and morphology of teeth, including restoring the loss of mineralized substance due to carries or resulting from an external trauma. Direct restoration is performed by placing a malleable filling material into a prepared tooth, followed by the in situ setting of the material.

Ideally, the restoration material should possess several properties, including adequate adhesive ability, insolubility, dimensional stability, biocompatibility, bioactivity and suitable mechanical properties. Various types of filling material are available, among which calcium silicate-based cements.

The implementation of the dental restoration material often requires a first phase of preparation by the practitioner of the filling material, followed by a period of in situ hardening. This is especially the case when using a hydraulic dental cement, such as a calcium silicate-based cement, which has to be exposed to water, usually by mixing an anhydrous powder cement phase with an aqueous liquid phase, in order to initiate hardening.

The main parameters to be controlled when providing a dental calcium silicate-based cement comprise the handling properties, the setting time and the mechanical properties of the hardened material.

Regarding the handling properties, the texture of the filling material has to be creamy for a good handling by the practitioner. Further, the working time should be just sufficient to enable the preparation of the filling material and its placement where restoration is needed.

The setting time should ideally be relatively short. Indeed, a too long setting time would be uncomfortable for the patient, may lead to the washout of the restorative material by saliva and to the irritation of oral tissues.

The hardened restoration material should have mechanical properties similar to those of the teeth. Especially, the compressive strength has to be sufficient to avoid breakage of the restorative material and ensure its longevity.

Mineral trioxide aggregate (MTA) is a dental calcium silicate-based cement introduced more than 25 years ago. Despite its good clinical efficacy, MTA presents drawbacks preventing its use for many cases. The major ones being very long setting time (about 3-4 hours) and its poor handling properties.

Sanaee et al. studied the influence on setting time of the particles size of a formulated MTA (Sanaee et al., "*The influence of particle size and multi-walled carbon nanotube*

*on physical properties of mineral trioxide aggregate*", Mater. Res. Express, 2019, Vol. 6(6), 065413). The formulated MTA used in this study had a setting time of about 65 min. They evidence that the setting time could be accelerated to about 12 min by reducing the particle size distribution by milling the MTA powder before use. Nevertheless, the decrease of the particle size distribution had a negative impact on compressive and flexural strengths. The addition of multi-walled carbon nanotubes enabled improve mechanical strength by restoring flexural strength, but with no significant impact on compressive strength.

The Applicant has previously provided bioactive and biocompatible dental restoration materials, as described in U.S. Pat. No. 7,819,663 and in U.S. Pat. No. 8,974,586, obtained from calcium silicate-based cements, and having good mechanical properties. Especially, the Applicant developed Biodentine® restorative material, a bioactive calcium silicate-based cement that sets in only 10-12 minutes, that is easy to handle and that have similar mechanical properties and mechanical behaviour as human dentin.

There is still a need for patients and practitioners to have restorative materials that harden faster once placed in the patient's mouth while keeping good handling properties for the practitioner (creamy texture, working time, etc. . . . ) and mechanical properties, especially compressive strength, at least as good as currently available products.

The Applicant herein evidences that using ultrafine calcium silicate (UCS) particles in a calcium silicate-based cement powder composition, in presence of a limited amount of water, strongly decrease the setting time while retaining good compressive strength of the resulting restorative material. The UCS particles used in the dental hydraulic cement of the invention have finely tuned $d_{10}$, $d_{50}$ and $d_{90}$ sizes, and specific area. The substitution of all or part of calcium silicate particles, especially C3S particles, in calcium silicate-based cements, by the UCS particles of the invention, also enable to keep good handling properties and satisfactory appearance.

SUMMARY

The present invention relates to a kit for producing a dental restoration material, said kit comprising:
- a first container containing a powder phase comprising:
  - from 15% to 98% in weight of the total weight of the powder phase of ultrafine particles of calcium silicate having a $d_{10}$ size ranging from 0.4 μm to 0.9 μm, preferably ranging from 0.4 μm to 0.8 μm, or ranging from 0.4 μm to 0.7 μm; a $d_{50}$ size ranging from 0.7 μm to 2.9 μm, preferably ranging from 0.8 μm to 2.5 μm, preferably 1 μm to 2.1 μm; and a $d_{90}$ size ranging from 1.3 μm to 7.0 μm, preferably ranging from 1.5 μm to 7 μm or ranging from 2 μm to 5 μm; wherein the $d_{10}$, $d_{50}$ and $d_{90}$ sizes are measured by laser diffraction;
  - from 2% to 35% in weight of the total weight of the powder phase of a radiopacifier; and
  - optionally one or more additive selected from setting accelerators, pigments, water reducing agents, texturing agents, pH stabilizing agents, surfactants, and fillers; and
- a second container containing an aqueous liquid phase;
- and wherein the weight ratio of the powder phase present in the kit to the liquid phase present in the kit ranges from 2 to 5; preferably from 2.5 to 4.0.

In one embodiment, the first container containing the powder phase comprises:

from 15% to 98% in weight of the total weight of the powder phase of ultrafine particles of calcium silicate having a $d_{10}$ size ranging from 0.5 μm to 0.9 μm, preferably from 0.5 μm to 0.8 μm, even more preferably from 0.5 μm to 0.7 μm; a $d_{50}$ size ranging from 0.7 μm to 2.9 μm, preferably ranging from 0.8 μm to 2.5 μm, preferably ranging from 1 μm to 2.1 μm; and a $d_{90}$ size ranging from 1.3 μm to 7.0 μm, preferably ranging from 1.5 μm to 7 μm or ranging from 2 μm to 5 μm; wherein the $d_{10}$, $d_{50}$ and $d_{90}$ sizes are measured by laser diffraction.

In one embodiment, the calcium silicate is selected from tricalcium silicate (C3S), dicalcium silicate (C2S) and any combinations thereof; preferably the calcium silicate is tricalcium silicate.

In one embodiment, the powder phase comprises a Portland cement and/or mineral trioxide aggregates (MTA), as ultrafine calcium silicate particles.

In one embodiment, the powder phase further comprises non-ultrafine particles of calcium silicate. In one embodiment, the amount of ultrafine calcium silicate particles ranges from 10% to 100% by weight to the total weight of calcium silicate present in the powder phase; preferably ranges from 10% wt to 70% wt; more preferably from 10% wt to 50% wt.

In one embodiment, the radiopacifier is selected from zirconium oxide, bismuth oxide, cerium oxide, barium sulphate, calcium tungstate, titanate dioxide, ytterbium oxide and mixtures thereof; preferably the radiopacifier is zirconium oxide.

In one embodiment, the powder phase comprises one or more additive, wherein the additive is selected from setting accelerators, such as calcium carbonate, calcium oxide, calcium phosphate and mixture thereof; and pigments, such as iron oxides.

In one embodiment, the powder phase comprises:

from 20% to 60% in weight of the total weight of the powder phase of ultrafine particles of tricalcium silicate having:

a specific area, measured by BET technique, ranging from 3 to 11 m²/g;

a $d_{10}$ size ranging from 0.4 μm to 0.9 μm, preferably ranging from 0.4 μm to 0.82 μm, ranging from 0.4 μm to 0.8 μm or ranging from 0.4 μm to 0.7 μm;

a $d_{50}$ size ranging from 0.7 μm to 2.9 μm, preferably ranging from 0.8 μm to 2.5 μm, preferably 1 μm to 2.1 μm or ranging from 0.8 μm to 2.1 μm; and a $d_{90}$ size ranging from 1.3 μm to 7.0 μm, preferably ranging from 1.4 μm to 7 μm, from 1.5 μm to 7 μm or ranging from 2 μm to 5 μm;

wherein the $d_{10}$, $d_{50}$ and $d_{90}$ sizes are measured by laser diffraction;

from 0% to 50% in weight of the total weight of the powder phase of non-ultrafine particles of calcium silicate;

from 2% to 35% in weight of the total weight of the powder phase of a radiopacifier; and from 0% to 25% in weight of the total weight of the powder phase of one or more setting accelerator such as calcium carbonate, calcium oxide and mixture thereof.

In one embodiment, the powder phase comprises:

from 20% to 60% in weight of the total weight of the powder phase of ultrafine particles of tricalcium silicate having:

a specific area, measured by BET technique, ranging from 3 to 11 m²/g;

a $d_{10}$ size ranging from 0.5 μm to 0.9 μm, preferably from 0.5 μm to 0.8 μm, even more preferably from 0.5 μm to 0.7 μm;

a $d_{50}$ size ranging from 0.7 μm to 2.9 μm, preferably ranging from 0.8 μm to 2.5 μm, preferably ranging from 1 μm to 2.1 μm, or ranging from 0.8 μm to 2.1 μm; and a $d_{90}$ size ranging from 1.3 μm to 7.0 μm, preferably ranging from 1.5 μm to 7 μm or ranging from 2 μm to 5 μm.

In one embodiment, the aqueous liquid phase is water. In one embodiment, the aqueous liquid phase further comprises one or more additive, wherein the additive is selected from setting accelerators, such as calcium chloride; and water reducing agents, such as a modified polycarboxylate.

In one embodiment, the aqueous liquid phase comprises:

from 60% to 85% in weight of the total weight of the aqueous liquid phase of water;

from 5% to 35% in weight of the total weight of the aqueous liquid phase of setting accelerator, preferably calcium chloride; and from 0% to 5% in weight of the total weight of the aqueous liquid phase of water reducing agent, preferably a modified polycarboxylate.

The invention also relates to a dental composition obtained by mixing the whole content of the first container with the whole content of the second container of the kit according to the invention.

In one embodiment, the composition has a setting time ranging from 1 min to 12 min, preferably from 4 min to 9 min.

In one embodiment, the dental composition has a compressive strength at 24 hours of more than 100 MPa; preferably more than 150 MPa.

The invention further relates to a medical device comprising the kit according to the invention; preferably the medical device is an injection system; more preferably is a syringe.

DETAILED DESCRIPTION

Figure 1:
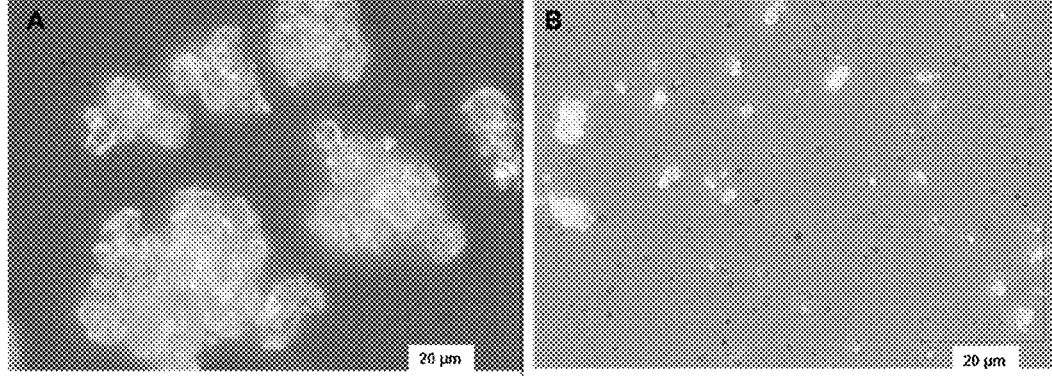
FIG. 1 is a set of microscopy clichés showing (A) coarsely grinded C3S particles and (B) ultrafine C3S particles.

In the present invention, the following terms have the following meanings:

"About" preceding a figure means plus or less 10% of the value of said figure.

"Additive" refers to any substance added, preferably in a low amount, in a composition for improving its physicochemical properties depending on its use. The additive may for example be selected from radiopacifiers (such as zirconium oxide), setting accelerators (such as calcium oxide, calcium carbonate, calcium chloride), pigments (such as iron oxides), water reducing agents (such as modified polycarboxylates), texturing agents, pH stabilizing agents, surfactants, fillers, and mixtures thereof.

"Alcohol" refers to any chemical compound having a hydroxyl function (—OH).

"Aqueous" refers to any compound or composition comprising water and/or moisture.

"BET" refers to any techniques based on the Brunauer-Emmet-Teller theory explaining the physical adsorption of a gas on a solid surface. According to one embodiment, the BET technique is used for determining the surface area (expressed in $m^2/g$) of a solid sample, preferably of a particle. According to one embodiment, the BET technique is carried out by a particle size analyzer such as Gemini 2375® or Gemini V® of the firm Micromeritics.

"Calcium silicate" refers to compounds that can be produced by reacting calcium oxide and silica in various ratios. According to one embodiment, the expression "calcium silicate" refers to compounds made of calcium and silicate, preferably selected from tricalcium silicate, dicalcium silicate or any mixtures thereof; more preferably tricalcium silicate C3S (of formula $Ca_3SiO_5$), dicalcium silicate C2S (of formula $Ca_2SiO_4$), or any mixtures thereof.

"Calcium silicate mixture" refers, according to one embodiment, to the total calcium silicate present in the solid phase according to the invention, said calcium silicate being under the form of ultrafine and/or non-ultrafine calcium silicate particles. According to one embodiment, the expression "calcium silicate mixture" refers to calcium silicate compound(s) as defined above, i.e. tricalcium silicate, dicalcium silicate or any mixtures thereof. According to one embodiment, the expression "calcium silicate mixture" refers to a mixture of calcium silicate compounds as defined above, wherein the calcium silicate compounds are under the form of ultrafine and/or non-ultrafine calcium silicate particles. According to one embodiment, the "calcium silicate mixture" may comprise calcium silicate being parts of a Portland cement and/or MTA.

"Calcium silicate particle": refers to an assembly comprising one or more calcium silicate compounds. The terms "calcium silicate particle" also include assemblies consisting of one or more calcium silicate compounds.

"Coarsely grinded particles" refers to particles having a $d_{10}$ size ranging from more than 1.7 up to 5 μm; a $d_{50}$ size ranging from more than 8 up to 14 μm and a $d_{90}$ size ranging from more than 20 up to 40 μm; and a specific area ranging from 0.3 to 1.2 $m^2/g$.

"Crushed particles" refers to particles having a $d_{10}$ size ranging from more than 2 up to 6 μm; a $d_{50}$ size ranging from more than 17 up to 25 μm and a $d_{90}$ size ranging from more than 150 up to 330 μm; and a specific area of about 0.5 $m^2/g$.

"Dental cement" refers to any composition suitable for restorative dentistry that acts as an adhesive to hold together the casting to the tooth structure.

"Dental composition" refers to any formulation suitable for dental applications.

"Dual syringe" refers to an injection system comprising or consisting of a mixing system and/or a mixing chamber, two cartridges and a plunger.

"$d_{10}$ size" means that 10% of the particles have a mean diameter less than said value. According to one embodiment, the $d_{10}$ size is measured by laser diffraction.

"$d_{50}$ size" means that 50% of the particles have a mean diameter less than said value. According to one embodiment, the $d_{50}$ size is measured by laser diffraction.

"$d_{90}$ size" means that 90% of the particles have a mean diameter less than said value. According to one embodiment, the $d_{90}$ size is measured by laser diffraction.

"Glycol" or "diol": refers to any compound having two hydroxyl groups carried out by different carbon atoms. According to one embodiment, the term "glycol" includes vicinal diol, i.e. compound having two hydroxyl group carried out by two adjacent carbon atoms. Examples of glycols include ethylene glycol, propylene glycol and polyethylene glycol.

"Ethylene glycol": refers to the glycol of formula HO—$(CH_2)_2$—OH.

"Fast hardening": refers to a compound or a composition able to harden after its hydration, in less than 12 min; preferably in less than 9 min.

"Grinding beads": refer to physical elements under the form of inert particles that are located in a grinding apparatus, and allow mechanically breaks a solid material into smaller pieces.

"Grinding chamber": refers to the part of a grinding apparatus in which are introduced the solid sample to be break into smaller pieces.

"Grinding time": refers to the time during which breaking a solid sample into smaller pieces, is implemented.

"Hardened dental material": refers to a material suitable for dental applications that is under a solid form. According to one embodiment, the expression "hardened dental material" refers to the material obtained after the hardening (or setting) of the dental composition of the invention. A "hardened dental filling material" especially refers to a hardened dental material suitable for filling dental restoration.

"Hydraulic cement": refers to a cement able to self-harden when contacted with water.

"Laser diffraction analysis": refers to a technique using diffraction patterns of a laser beam passed through a particulate object for determining its size.

"Medical device": refers to any apparatus, material or object used alone or in combination, which may be used for diagnostic and/or therapeutic purposes.

"Metal oxide": refers to chemical compounds comprising or consisting of a metal cation and an oxide anion.

"Micronized particles" refers to particles having a $d_{10}$ size ranging from more than 0.7 up to 1.7 μm; a $d_{50}$ size ranging from more than 2.9 up to 8 μm and a $d_{90}$ size ranging from more than 6 up to 20 μm; and a specific area ranging from 0.8 to 3 $m^2/g$.

"Modified polycarboxylate": refers to any polymer having as repeating unit, a moiety comprising at least on carboxylate function, and wherein a part or all of said carboxylate functions have been modified for providing another chemical function. According to one embodiment, the expression "modified polycarboxylate" refers to any polymer comprising at least two carboxylate functions on its backbone, and wherein a part or all of said carboxylate functions have been modified for providing another chemical function. According to one embodiment, the expression "modified polycarboxylate" refers to a polymer with multiple carboxylate functions in which a part or all of said carboxylate functions have reacted with one functional group of a chemical component, said functional group being selected from amine, hydroxyl, nitrile and halo.

"MTA" or "Mineral Trioxide Aggregate: refers to a hydraulic cement comprising Portland cement combined with a radiopacifier which can be for example bismuth oxide. According to one embodiment, the term "MTA" refers to a hydraulic cement comprising tricalcium silicate, dicalcium silicate, tricalcium aluminate, tetracalcium aluminoferrite, calcium sulfate and a radiopacifier such as bismuth oxide.

"Non-aqueous" (see also "water-free) refers to any compound or composition free of water and/or moisture.

"Pigment": refers to any coloring chemical compound that may be natural or synthetic, mineral or organic.

"Polyethylene glycol" or "polyethylene oxide": refers to a polymer which is a polyether compound of general formula H—[O—$CH_2$—$CH_2$]~—OH wherein n is a positive integer.

"Portland cement": refers to a hydraulic material comprising at least two-thirds by mass of calcium silicates, ($3CaO \cdot SiO_2$, and $2CaO \cdot SiO_2$) as main component, and comprising additional compounds including aluminum- and/or iron-containing clinker phases (for example, tricalcium aluminate and tetracalcium aluminoferrite). The expression "Portland cement" includes all the Portland cement compositions well-known by the skilled artisan such as those defined by the European EN 197 norm, and by the International ASTM C150 norm.

"Radiopacifying agent" or "radiopacifier": refers to a substance added to a material in order to make it opaque, especially to make it visible under X-ray imaging.

"Setting accelerator" refers to any agent which reduces the setting time of a material when added to said material compared to the setting time of the same material without said agent.

"Setting time" herein refers to the period of time needed for a dental composition of the invention to be totally hardened after its hydration. The setting time starts when placing the tested composition in defined conditions of temperature and hygrometry (typically water bath at 37° C.). The setting time may be measured by several methods such as for example a Gillmore apparatus (Gillmore needle) or a Vicat apparatus (Vicat needle). For example; the setting time may be measured using a Gillmore apparatus: the material to be tested is placed into a mold which is introduced in a water bath at 37° C., the setting of the material is assessed using a Gillmore needle of 400 g, and the material is considered as being set when the needle leaves no trace on the surface of the mold. The setting time corresponds to the period of time between the placement of the molds into the water bath and the observed setting.

"Size": refers to the average diameter of a particle.

"Specific area" or "specific surface": refers to the ratio of the area of the actual surface of an object and the amount of substance for said object. The specific area is expressed in square meter by gram ($m^2/g$). According to one embodiment, the specific surface is measured by BET (Brunauer, Emmett and Teller technique).

"Subject": refers to a warm-blooded animal, more preferably a human. Preferably, the subject is a patient, i.e. the subject is awaiting the receipt of, or is receiving medical care or is/will be the object of a medical procedure.

"Texturing agent": refers to any compound which, when added to a substance, enhances the viscosity and the cohesion of said substance.

"Treatment" or "Treating": refers to therapeutic treatment wherein the object is to cure or slow down (lessen) the targeted pathologic condition or disorder. A subject or mammal is successfully "treated" for the condition or disorder if, after receiving the dental composition or hardened dental material of the present invention, the patient shows observable and/or measurable reduction in one or more of the symptoms associated with the specific disease or condition; and improvement in quality of life issues. The above parameters for assessing successful treatment and improvement in the disease or conditions are readily measurable by routine procedures familiar to a physician.

"Ultrafine particles": refers to particles having a $d_{10}$ size of less than 0.7 μm; a $d_{50}$ size ranging from about 0.7 μm to 2.9 μm and a $d_{90}$ size ranging from about 2.0 μm to 7.0 μm; and a specific area measured by BET, ranging from about 3 to 11 $m^2/g$. According to one embodiment, the $d_{10}$, $d_{50}$ and $d_{90}$ sizes are measured by laser diffraction. According to one embodiment, the ultrafine particles also refers to particles having a $d_{10}$ size ranging from 0.4 μm to 0.9 μm, preferably ranging from 0.4 μm to 0.82 μm or 0.4 μm to 0.8 μm; a $d_{50}$ size ranging from 0.7 μm to 2.9 μm; and a $d_{90}$ size ranging from 1.3 μm to 7 μm. According to one embodiment, the ultrafine particles have a $d_{10}$ size ranging from 0.4 μm to 0.8 μm; a $d_{50}$ size ranging from 0.8 μm to 2.1 μm; and a $d_{90}$ size ranging from 1.4 μm to 7 μm; and a specific area measured by BET, ranging from about 3 to 11 $m^2/g$.

"Water-free" (see also "non-aqueous"): refers to any non-aqueous or non-hydrated compound, phase or material. According to one embodiment, the term "non-hydrated" further means that said compound or material has not been contacted with any water molecule.

"Water-reducing agent": refers to a substance able to improve the rheological properties of a composition. Especially, the "water-reducing agent" may be a plastifying or fluidifying agent.

"Working time" refers to the period of time during which the practitioner can work the dental composition until its placement into the oral cavity of a subject in need thereof. In one embodiment, the working time corresponds to the period of time between the end of mixture of the calcium silicate phase with the aqueous phase and the beginning of the hardening, when the composition becomes too consistent to be manipulated by the practitioner. Preferably, the working time is of more than 1 minute.

Further, in the present invention, when referring to a range, the following is meant: "ranging from X to Y" means that X and Y are included in the range; "ranging from more than X, up to Y" means that X is not included in the range while Y is included in the range; and "less than X" means that the range includes X or lower values.

This invention thus relates to the provision of a dental restoration material, obtained from a dental hydraulic cement, namely a calcium silicate-based cement, having short setting time and a good compressive strength once hardened.

The invention also relates to the provision of starting compositions enabling to produce the dental restoration material of the invention. In one embodiment, it is thus provided a calcium silicate anhydrous phase suitable to produce the dental restoration material of the invention.

The solution of the invention includes using ultrafine calcium silicate particles (hereafter referred to as "UCS particles") in the calcium silicate anhydrous phase, the UCS particles having finely tuned granulometry, and to adjust the other components so that the amount of water required to set the hydraulic cement remains low.

The properties of suitable UCS particles are first detailed. Then, the content of the starting compositions and kits suitable to provide the expected dental restoration material are described. The properties of the resulting dental restoration material are also discussed as well as possible uses.

UCS Particles

In one embodiment, the invention relates to ultrafine particles of calcium silicate (UCS particles).

According to one embodiment, the calcium silicate of the UCS particles of the invention is selected from tricalcium silicate, dicalcium silicate or any mixtures thereof; preferably is tricalcium silicate (C3S). According to one embodiment, tricalcium silicate is selected from compound of formula $Ca_3SiO_5$ (also noted as "C3S") and of formula $Ca_3Si_3O_9$ (also called "calcium oxosilanediolate"). According to one embodiment, dicalcium silicate is compound of formula $Ca_2SiO_4$ (also noted as "C2S").

In one embodiment, the calcium silicate of the UCS particles of the invention may be the calcium silicate present in a Portland cement. In another embodiment, the calcium silicate of the UCS particles of the invention may be the calcium silicate present in mineral trioxide aggregate (MTA).

According to one embodiment, the UCS particles of the invention are under the form of a powder.

In an embodiment, the UCS particles of the invention can be characterized by their particle size distribution, especially by their $d_{10}$, $d_{50}$ and/or $d_{90}$ sizes. According to one embodiment, the $d_{10}$, $d_{50}$ and $d_{90}$ sizes are measured by laser diffraction.

D90 According to one embodiment, the UCS particles have a $d_{90}$ size ranging from 1.4 μm to 6.0 μm, preferably from 1.4 to 5.0 μm, more preferably from 1.4 to 3.5 μm. In one embodiment, the UCS particles have a $d_{90}$ size ranging from 1.4 μm to 5.9 μm, from 1.4 μm to 5.8 μm, from 1.4 μm to 5.7 μm, from 1.4 μm to 5.6 μm, from 1.4 μm to 5.5 μm, from 1.4 μm to 5.4 μm, from 1.4 μm to 5.3 μm, from 1.4 μm to 5.2 μm, from 1.4 μm to 5.1 μm, from 1.4 μm to 5.0 μm, from 1.4 μm to 4.9 μm, from 1.4 μm to 4.8 μm, from 1.4 μm to 4.7 μm, from 1.4 μm to 4.6 μm, from 1.4 μm to 4.5 μm, from 1.4 μm to 4.4 μm, from 1.4 μm to 4.3 μm, from 1.4 μm to 4.2 μm, from 1.4 μm to 4.1 μm, from 1.4 μm to 4.0 μm, from 1.4 μm to 3.9 μm, from 1.4 μm to 3.8 μm, from 1.4 μm to 3.7 μm, from 1.4 μm to 3.6 μm, from 1.4 μm to 3.5 μm, from 1.4 μm to 3.4 μm, from 1.4 μm to 3.3 μm, from 1.4 μm to 3.2 μm, from 1.4 μm to 3.1 μm, from 1.4 μm to 3.0 μm, from 1.4 μm to 2.9 μm, from 1.4 μm to 2.8 μm, from 1.4 μm to 2.7 μm, from 1.4 μm to 2.6 μm, from 1.4 μm to 2.5 μm, from 1.4 μm to 2.4 μm, from 1.4 μm to 2.3 μm, from 1.4 μm to 2.2 μm, from 1.4 μm to 2.1 μm, from 1.4 μm to 2.0 μm, from 1.4 μm to 1.9 μm, from 1.4 μm to 1.8 μm, from 1.4 μm to 1.7 μm, from 1.4 μm to 1.6 μm, from 1.4 μm to 1.5 μm. According to one embodiment, the UCS particles have d90 size ranging from 1.3 μm to 7 μm, preferably from 1.4 μm to 7 μm; preferably from 1.4 μm to 6 μm; more preferably from 2 μm to 5 μm; even more preferably from 2.05 μm to 4.55 μm. According to one embodiment, the UCS particles have d90 size of 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 μm. According to one embodiment, the UCS particles have a $d_{90}$ size ranging from 1.5 μm to 6.0 μm, preferably from 2 μm to 6 μm, from 2.5 μm to 6 μm, from 3 μm to 6 μm, from 3.5 μm to 6 μm, from 4 μm to 6 μm, from 4.5 μm to 6 μm, or from 5 μm to 6 μm. According to one embodiment, the UCS particles have d90 size ranging from 2 μm to 4.6 μm, preferably from 2 μm to 4.7 μm, from 2 μm to 4.8 μm, or from 2 μm to 4.9 μm. According to one embodiment, the UCS particles have a $d_{90}$ size of 2.05 μm, 2.47 μm, 3.12 μm or 4.55 μm.

According to one embodiment, the UCS particles have d90 size ranging from 1.5 μm to 2 μm. According to one embodiment, the UCS particles have d90 size of 1.51; 1.52; 1.53; 1.54; 1.55; 1.56; 1.57; 1.58; 1.59; 1.60; 1.61; 1.62; 1.63; 1.64; 1.65; 1.66; 1.67; 1.68; 1.69; 1.70; 1.71; 1.72; 1.73; 1.74; 1.75; 1.76; 1.77; 1.78; 1.79; 1.80; 1.81; 1.82; 1.83; 1.84; 1.85; 1.86; 1.87; 1.88; 1.89; 1.90; 1.91; 1.92; 1.93; 1.94; 1.95; 1.96; 1.97; 1.98; 1.99; 2.00; 2.01; 2.02; 2.03; 2.04; 2.05 μm. According to one embodiment, the UCS particles have d90 size ranging from 4 to 7 μm. According to one embodiment, the UCS particles have d90 size of 4.0; 4.1; 4.2; 4.3; 4.4; 4.5; 4.6; 4.7; 4.8; 4.9; 5.0; 5.1; 5.2; 5.3; 5.4; 5.5; 5.6; 5.7; 5.8; 5.9; 6; 6.1; 6.2; 6.3; 6.4; 6.5; 6.6; 6.7; 6.8; 6.9 or 7.0 pam.

According to one embodiment, the UCS particles have a $d_{90}$ size ranging from 1.3 μm to 6.0 μm, preferably from 1.3 to 5.0 μm, more preferably from 1.3 to 3.5 μm. In one embodiment, the UCS particles have a $d_{90}$ size ranging from 1.3 μm to 5.9 μm, from 1.3 μm to 5.8 μm, from 1.3 μm to 5.7 μm, from 1.3 μm to 5.6 μm, from 1.3 μm to 5.5 μm, from 1.3 μm to 5.4 μm, from 1.3 μm to 5.3 μm, from 1.3 μm to 5.2 μm, from 1.3 μm to 5.1 μm, from 1.3 μm to 5.0 μm, from 1.3 μm to 4.9 μm, from 1.3 μm to 4.8 μm, from 1.3 μm to 4.7 μm, from 1.3 μm to 4.6 μm, from 1.3 μm to 4.5 μm, from 1.3 μm to 4.4 μm, from 1.3 μm to 4.3 μm, from 1.3 μm to 4.2 μm, from 1.3 μm to 4.1 μm, from 1.3 μm to 4.0 μm, from 1.3 μm to 3.9 μm, from 1.3 μm to 3.8 μm, from 1.3 μm to 3.7 μm, from 1.3 μm to 3.6 μm, from 1.3 μm to 3.5 μm, from 1.3 μm to 3.4 μm, from 1.3 μm to 3.3 μm, from 1.3 μm to 3.2 μm, from 1.3 μm to 3.1 μm, from 1.3 μm to 3.0 μm, from 1.3 μm to 2.9 μm, from 1.3 μm to 2.8 μm, from 1.3 μm to 2.7 μm, from 1.3 μm to 2.6 μm, from 1.3 μm to 2.5 μm, from 1.3 μm to 2.4 μm, from 1.3 μm to 2.3 μm, from 1.3 μm to 2.2 μm, from 1.3 μm to 2.1 μm, from 1.3 μm to 2.0 μm, from 1.3 μm to 1.9 μm, from 1.3 μm to 1.8 μm, from 1.3 μm to 1.7 μm, from 1.3 μm to 1.6 μm, from 1.3 μm to 1.5 μm.

D50

According to one embodiment, the UCS particles have a $d_{50}$ size ranging from 0.7 μm to 2.9 μm, preferably from 0.7 μm to 2.0 μm, preferably from 0.7 μm to 1.5 μm. According to one embodiment, the UCS particles have a $d_{50}$ size ranging from 0.7 μm to 2.8 μm, from 0.7 μm to 2.7 μm, from 0.7 μm to 2.6 μm, from 0.7 μm to 2.5 μm, from 0.7 μm to 2.4 μm, from 0.7 μm to 2.3 μm, from 0.7 μm to 2.2 μm, from 0.7 μm to 2.1 μm, from 0.7 μm to 2.0 μm, from 0.7 μm to 1.9 μm, from 0.7 μm to 1.8 μm, from 0.7 μm to 1.7 μm, from 0.7 μm to 1.6 μm, from 0.7 μm to 1.5 μm, from 0.7 μm to 1.4 μm, from 0.7 μm to 1.3 μm, from 0.7 μm to 1.2 μm, from 0.7 μm to 1.1 μm, from 0.7 μm to 1.0 μm, from 0.7 μm to 0.9 μm, from 0.7 μm to 0.8 μm. According to one embodiment, the UCS particles have a $d_{50}$ size ranging from 0.8 μm to 2.9 µm; preferably ranging from 0.8 µm to 2.1 µm; preferably from 1.5 µm to 2.1 µm; preferably from 1.04 µm to 2.1 µm; more preferably from 1 µm to 2.1 µm or from 1.04 µm to 1.93 µm. According to one embodiment, the UCS particles have a $d_{50}$ size ranging from 1 µm to 2.9 µm, preferably from 1 µm to 2.8 µm; from 1 µm to 2.7 µm; from 1 µm to 2.6 µm; from 1 µm to 2.5 µm; from 1 µm to 2.4 µm; from 1 µm to 2.3 µm; from 1 µm to 2.2 µm; from 1 µm to 2.1 µm; from 1 µm to 2.0 µm; from 1 µm to 1.9 µm; from 1 µm to 1.8 µm; from 1 µm to 1.7 µm; from 1 µm to 1.6 µm; or from 1 µm to 1.5 µm. According to one embodiment, the UCS particles have a $d_{50}$ size ranging from 1.1 µm to 2.9 µm, preferably from 1.2 µm to 2.9 µm; from 1.3 µm to 2.9 µm; from 1.4 µm to 2.9 µm; from 1.5 µm to 2.9 µm; from 1.6 µm to 2.9 µm; from 1.7 µm to 2.9 µm; from 1.8 µm to 2.9 µm; from 1.9 µm to 2.9 µm; from 2 µm to 2.9 µm; from 2.1 µm to 2.9 µm; from 2.2 µm to 2.9 µm; from 2.3 µm to 2.9 µm; or from 2.4 µm to 2.9 µm. According to one embodiment, the UCS particles have a $d_{50}$ size of 1.04 µm, 1.29 µm, 1.50 µm or 1.93 µm. According to one embodiment, the UCS particles have a $d_{50}$ size of 0.80: 0.81; 0.82; 0.83; 0.84; 0.85; 0.86; 0.87; 0.88; 0.89; 0.90; 0.91; 0.92; 0.93; 0.94; 0.95; 0.96; 0.97; 0.98; 0.99; or 1 µm.

D10

According to one embodiment, the UCS particles have a $d_{10}$ size of less than 0.7 µm, preferably ranging from 0.1 µm to 0.7 µm; preferably from 0.2 µm to 0.6 µm; from 0.3 µm to 0.55 µm; from 0.35 µm to 0.50 µm; from 0.40 µm to 0.50 µm.

According to one embodiment, the UCS particles have a $d_{10}$ size ranging from 0.4 µm to 0.9 µm; preferably from 0.5 µm to 0.9 µm, from 0.4 µm to 0.85 µm; from 0.4 µm to 0.82 µm or from 0.5 µm to 0.85 µm; more preferably from 0.4 µm to 0.82 µm, from 0.4 µm to 0.8 µm or from 0.4 µm to 0.7 µm. According to one embodiment, the UCS particles have a $d_{10}$ size ranging from 0.4 µm to 0.6 µm, more preferably from 0.4 µm to 0.5 µm. According to one embodiment, the UCS particles have a $d_{10}$ size ranging from 0.5 µm to 0.9 µm, from 0.6 µm to 0.9 µm, from 0.7 µm to 0.9 µm or from 0.8 µm to 0.9 µm. According to one embodiment, the UCS particles have a $d_{10}$ size of 0.5 µm; 0.51; 0.52; 0.53; 0.54; 0.55; 0.56; 0.57; 0.58; 0.59; 0.60; 0.61; 0.62; 0.63; 0.64; 0.65; 0.66; 0067; 0.68; 0.69; 0.70; 0.71; 0.72; 0.73; 0.74; 0.75; 0.76; 0.77; 0.78; 0.79; 0.80; 0.81; or 0.82 µm.

According to one embodiment, the UCS particles are characterized by:
a $d_{50}$ size ranging from 0.7 µm to 2.9 µm; and
a $d_{90}$ size ranging from 1.4 µm to 6.0 µm;
wherein the $d_{50}$ and $d_{90}$ sizes are measured by laser diffraction.

According to one embodiment, the UCS particles are characterized by:
a $d_{50}$ size ranging from 0.4 µm to 0.9 µm, preferably from 0.4 µm to 0.82 µm or from 0.4 µm to 0.8 µm; even more preferably from 0.5 µm to 0.8 µm; and
a $d_{90}$ size ranging from 1.3 µm to 7.0 µm, preferably from 1.4 µm to 7 µm;
wherein the $d_{50}$ and $d_{90}$ sizes are measured by laser diffraction.

According to one embodiment, the UCS particles are characterized by:
a $d_{50}$ size ranging from 1 µm to 2.9 µm, preferably from 1 µm to 2.1 µm; and
a $d_{90}$ size ranging from 1.4 µm to 6.0 µm, preferably from 2 µm to 5 µm;
wherein the $d_{50}$ and $d_{90}$ sizes are measured by laser diffraction.

According to one embodiment, the UCS particles are characterized by:
a $d_{10}$ size of less than 0.7 µm;
a $d_{50}$ size ranging from 0.7 µm to 2.9 µm; and
a $d_{90}$ size ranging from 1.4 µm to 6.0 µm;
wherein the $d_{10}$, $d_{50}$ and $d_{90}$ sizes are measured by laser diffraction.

According to one embodiment, the UCS particles are characterized by:
a $d_{10}$ size ranging from 0.1 µm to 0.7 µm;
a $d_{50}$ size ranging from 0.7 µm to 2.9 µm; and
a $d_{90}$ size ranging from 1.4 µm to 6.0 µm;
wherein the $d_{10}$, $d_{50}$ and $d_{90}$ sizes are measured by laser diffraction.

According to one embodiment, the UCS particles are characterized by:
a $d_{10}$ size ranging from 0.5 µm to less than 0.7 µm, a $d_{50}$ size ranging from 0.7 µm to 2.9 µm, preferably from 1 µm to 2.1 µm; and
a $d_{90}$ size ranging from 1.4 µm to 6.0 µm, preferably from 2 µm to 5 µm;
wherein the $d_{10}$, $d_{50}$ and $d_{90}$ sizes are measured by laser diffraction.

According to one embodiment, the UCS particles are characterized by:
a $d_{10}$ size ranging from less than 0.7 µm to 0.9 µm, preferably from 0.7 µm to 0.9 µm;
a $d_{50}$ size ranging from 0.7 µm to 2.9 µm, preferably from 1 µm to 2.1 µm; and
a $d_{90}$ size ranging from 1.4 µm to 6.0 µm, preferably from 2 µm to 5 µm;
wherein the $d_{10}$, $d_{50}$ and $d_{90}$ sizes are measured by laser diffraction.

According to one embodiment, the UCS particles are characterized by:
a $d_{10}$ size ranging from 0.5 µm to 0.9 µm,
a $d_{50}$ size ranging from 1 µm to 2.1 µm and
a $d_{90}$ size ranging from 2.0 µm to 5.0 µm,
wherein the $d_{10}$, $d_{50}$ and $d_{90}$ sizes are measured by laser diffraction.

The UCS particles can also be characterized by the specific area. According to one embodiment, the UCS particles have a specific area, measured by BET (Brunauer, Emmett and Teller technique), ranging from 3 to 11 $m^2/g$; preferably from 3 to 9 $m^2/g$; preferably from 4 to 8 $m^2/g$, more preferably from 5 to 7 $m^2/g$. According to one embodiment, the UCS particles have a specific area, measured by BET, ranging from 4 to 11 $m^2/g$, from 5 to 11 $m^2/g$, from 6 to 11 $m^2/g$, from 7 to 11 $m^2/g$, from 8 to 11 $m^2/g$, from 9 to 11 $m^2/g$, from 10 to 11 $m^2/g$. According to one embodiment, the UCS particles have a specific area, measured by BET, ranging from 3 to 9 $m^2/g$; preferably from 3 to 8 $m^2/g$, 3 to 7 $m^2/g$, 3 to 6 $m^2/g$, from 3 to 5 $m^2/g$ or 3 to 4 $m^2/g$. According to one embodiment, the UCS particles have a specific area, measured by BET, of about 3, 4, 5, 6, 7, 8, 9, 10 or 11 $m^2/g$. According to one embodiment, the UCS particles have a specific area, measured by BET, ranging from 5 $m^2/g$ to 9 $m^2/g$., preferably from 5.17 $m^2/g$ to 8.72 $m^2/g$.

According to one embodiment, the UCS particles are characterized by:
a specific area, measured by BET, ranging from 3 to 11 $m^2/g$; and
d10, d50 and d90 as defined herein above.

According to one embodiment, the UCS particles are characterized by:

a specific area, measured by BET, ranging from 3 to 11 $m^2/g$;

a $d_{10}$ size of less than 0.7 $\mu m$;

a $d_{50}$ size ranging from 0.7 $\mu m$ to 2.9 $\mu m$; and a $d_{90}$ size ranging from 1.4 $\mu m$ to 6.0 $\mu m$;

wherein the $d_{10}$, $d_{50}$ and $d_{90}$ sizes are measured by laser diffraction.

According to one embodiment, the UCS particles are characterized by:

a specific area, measured by BET, ranging from 3 to 11 $m^2/g$;

a $d_{10}$ size ranging from 0.1 $\mu m$ to 0.7 $\mu m$;

a $d_{50}$ size ranging from 0.7 $\mu m$ to 1.5 $\mu m$; and a $d_{90}$ size ranging from 1.4 $\mu m$ to 3.5 $\mu m$;

wherein the $d_{10}$, $d_{50}$ and $d_{90}$ sizes are measured by laser diffraction.

According to one embodiment, the UCS particles are characterized by:

a specific area, measured by BET, ranging from 3 to 11 $m^2/g$, preferably from 5 to 9 $m^2/g$;

a $d_{10}$ size ranging from 0.5 $\mu m$ to 0.9 $\mu m$, a $d_{50}$ size ranging from 0.7 $\mu m$ to 2.9 $\mu m$, a $d_{90}$ size ranging from 1.4 $\mu m$ to 6.0 $\mu m$;

wherein the $d_{10}$, $d_{50}$ and $d_{90}$ sizes are measured by laser diffraction.

According to one embodiment, the UCS particles are characterized by:

a specific area, measured by BET, ranging from 3 to 11 $m^2/g$, preferably from 5 to 9 $m^2/g$;

a $d_{10}$ size ranging from 0.5 $\mu m$ to 0.9 $\mu m$, a $d_{50}$ size ranging from 1 $\mu m$ to 2.1 $\mu m$ and a $d_{90}$ size ranging from 2.0 $\mu m$ to 5.0 $\mu m$, wherein the $d_{10}$, $d_{50}$ and $d_{90}$ sizes are measured by laser diffraction.

The ultrafine UCS particles as defined above may be obtained by various processes of manufacturing.

According to a first embodiment, the UCS particles may be manufactured by a mechanical grinding process. According to one embodiment, the mechanical grinding process of the invention comprises:

(i) mixing crushed and/or coarsely grinded calcium silicate particles with a non-aqueous solvent, such as an alcohol, in a grinding chamber; and (ii) grinding the mixture obtained at step (i) with grinding beads, having preferably a diameter ranging from 0.4 mm to 3 mm.

According to one embodiment, the crushed and/or coarsely grinded calcium silicate particles used to manufacture the UCS particles of the invention are selected from crushed and/or coarsely grinded tricalcium silicate, dicalcium silicate or any mixtures thereof; preferably are crushed and/or coarsely grinded tricalcium silicate (C3S). In one embodiment, the crushed and/or coarsely grinded calcium silicate particles used to manufacture the UCS particles of the invention are the calcium silicate present in a Portland cement. In such case, crushed and/or coarsely grinded Portland cement is grinded so that the calcium silicate particles contained therein have the specifications of the UCS particles of the invention. In one embodiment, the crushed and/or coarsely grinded calcium silicate particles used to manufacture the UCS particles of the invention is the calcium silicate present in a mineral trioxide aggregate (MTA). In such case, crushed and/or coarsely grinded MTA is grinded so that the calcium silicate particles contained therein have the specifications of the UCS particles of the invention.

According to one embodiment, the non-aqueous solvent is an alcohol. In one embodiment, the alcohol is selected from primary, secondary or tertiary alcohol. According to one embodiment, alcohol is isopropanol.

According to one embodiment, the grinding chamber is not made of stainless steel in order to avoid blackening the powder and to prevent the contamination of the powder by the presence of traces if stainless steel. According to one embodiment, the grinding chamber is made of and/or coated with metal oxides, such as zirconium oxide; tungsten carbide and/or silicon carbide.

According to one embodiment, the grinding chamber is filled with 33% vol. of calcium silicate particles to grind and 66% vol. of alcohol. According to one embodiment, the grinding chamber is filled with 50% vol. of calcium silicate particles to grind and 50% vol. of alcohol.

According to one embodiment, step (i) is carried out by mixing crushed or coarsely grinded C3S particles with isopropanol, preferably in a grinding chamber of a grinding apparatus.

According to one embodiment, grinding step (ii) is a mechanical grinding. According to one embodiment, grinding is implemented by a grinding apparatus well-known by the skilled artisan such as for example, EMAX® of RETSCH.

According to one embodiment, the grinding beads are not made of stainless steel for the same reasons as detailed above. According to one embodiment, the grinding beads are made of and/or coated with metal oxides, such as zirconium oxide; tungsten carbide and/or silicon carbide.

According to one embodiment, the mean diameter of grinding beads ranges from 0.4 mm to 3 mm; preferably from 0.5 to 2.5 mm; from 0.5 to 2 mm; from 0.5 to 1.5 mm; or from 0.5 to 1 mm; or from 0.4 mm to 0.8 mm.

According to one embodiment, grinding is carried out during a time ranging from 1 min to 60 min, preferably from 10 min to 40 min; more preferably from 20 min to 30 min.

Such short time of grinding avoid contamination of the UCS particles powder by mineral or metallic elements of the grinding means.

According to one embodiment, grinding is carried out with a grinding rate ranging from more than 0 to 5000 rpm; preferably from 1000 rpm to 3000 rpm; more preferably is about 1900 rpm. According to one embodiment, grinding is carried out with a grinding rate ranging from 9 to 15 m/s.

According to one embodiment, the process of the invention is carried out with 45 g of coarsely grinded C3S particles, 30 mL of isopropanol and 90 g of grinding beads. According to one embodiment, the process of the invention is carried out with the apparatus EMAX® with a grinding rate of about 1900 rpm for 20 min.

According to one embodiment, the process of manufacturing of the UCS particles further comprises a drying step. According to one embodiment, drying step is carried out after step (ii). According to one embodiment, drying step allows removing alcohol such as isopropanol from the grinding mixture. According to one embodiment, drying step is carried out at a temperature ranging from 30° C. to 300° C.; preferably from 40° C. to 100° C.; more preferably is about 50° C. According to one embodiment, drying step is carried out at a temperature of about 90° C.

According to one embodiment, the process of the invention further comprises a sifting step. According to one embodiment, the sifting step is carried out by outing the grinding mixture obtained after step (ii) through a sieve.

The UCS particles as defined above may be used as setting accelerator; preferably as setting accelerator of a dental composition such as a hydraulic dental cement. In one embodiment, when used in a dental hydraulic cement, the UCS particles of the invention reduce the setting time of the cement by 10% to 70%, compared to the same dental hydraulic cement comprising only non-ultrafine calcium silicate particles; preferably by 30% to 65%; more preferably by 40% to 65%. According to one embodiment, when used in a dental hydraulic cement, the UCS particles of the invention reduce the setting time of the cement by about 10%, 15%, 20%, 25%, 30%, 35%, 40%, 45%, 50%, 60% or even 65% compared to the same dental hydraulic cement comprising only non-ultrafine calcium silicate particles.

Powder Phase and Aqueous Liquid Phase

The invention thus relates to the provision of starting compositions enabling to produce the dental restoration material of the invention, especially it is provided calcium silicate anhydrous phases comprising UCS particles.

In one embodiment, it is provided a powder phase comprising UCS particles, preferably an anhydrous powder phase comprising UCS particles, more preferably an anhydrous calcium silicate cement powder phase comprising UCS particles. In this embodiment, an aqueous phase, preferably an aqueous liquid phase, is also needed so that upon mixing with the powder phase comprising the UCS particles, the dental restoration material of the invention is obtained.

Powder Phase

In one embodiment, the powder phase of the invention comprises UCS particles as defined above.

In a preferred embodiment the powder phase is anhydrous or water-free. Indeed, in presence of water calcium silicate begins hardening. Therefore, it is important that the powder phase remains free of water during storage to avoid its undesirable setting at this stage.

According to one embodiment, the powder phase is a calcium silicate phase, preferably a calcium silicate-based cement phase. According to one embodiment, the powder phase comprises ultrafine and non-ultrafine calcium silicate particles. According to one embodiment, the powder phase does not comprise any aluminate, such as calcium aluminate. According to one embodiment, the powder phase does not comprise any halogen or halogenated compounds, such as for example fluoride. According to one embodiment, the powder phase does not comprise any phosphates such as for example calcium phosphate. According to one embodiment, the powder phase does not comprise any porous compounds. According to one embodiment, the powder phase does not comprise any porous fillers and/or porous fibers.

According to one embodiment, the powder phase comprises ultrafine calcium silicate particles as defined above and other components that are not under the form of ultrafine particles but as crushed, coarsely grinded and/or micronized particles. The "other components" of the powder phase may be additives as detailed below and/or non-ultrafine calcium silicate particles.

According to one embodiment, the powder phase comprises a calcium silicate mixture, wherein the calcium silicate mixture comprises (i) UCS particles of the invention and optionally (ii) non-ultrafine calcium silicate particles.

In the present invention, the expression "non-ultrafine calcium silicate particles" refers to calcium silicate particles that do not have the granulometry properties of above defined UCS particles, especially that do not have the $d_{10}$, $d_{50}$ and/or $d_{90}$ sizes nor the specific area as defined of the UCS particles. According to one embodiment, the non-ultrafine calcium silicate particles may be under the form of crushed, coarsely grinded and/or micronized calcium silicate particles. As for the UCS particles, the non-ultrafine calcium silicate particles are selected from tricalcium silicate particles, dicalcium silicate particles or any mixtures thereof.

According to one embodiment, the coarsely grinded calcium silicate particles are characterized by a $d_{10}$ size ranging from more than 1.7 up to 5 μm, preferably from more than 1.7 to 3 μm, more preferably of about 2.1 μm. According to one embodiment, the coarsely grinded calcium silicate particles are characterized by a $d_{50}$ size ranging from more than 8 up to 14 μm, preferably from more than 8 to 13 μm, more preferably of about 9.8 μm. According to one embodiment, the coarsely grinded calcium silicate particles are characterized by a $d_{90}$ size ranging from more than 20 μm to 40 μm, preferably from 25 to 35 μm, more preferably of about 28.0 μm. According to one embodiment, the coarsely grinded calcium silicate particles are characterized by a $d_{10}$ size of about 2.1 μm, a $d_{50}$ of about 9.8 μm and a $d_{90}$ of about 28.0 μm. According to one embodiment, the coarsely grinded calcium silicate particles are characterized by a $d_{10}$ size of 2.1 μm, a $d_{50}$ of 9.8 μm and a $d_{90}$ of 28.0 μm. According to one embodiment, the coarsely grinded calcium silicate particles are characterized by a specific surface measured by BET (Brunauer, Emmett and Teller technic) ranging from 0.3 to 1.2 m²/g, preferably from 0.5 to 1.5 m²/g, more preferably of about 0.78 m²/g. According to one embodiment, the coarsely grinded calcium silicate particles are characterized by a $d_{10}$ size of 2.1 μm, a $d_{50}$ of 9.8 μm and a $d_{90}$ of 28.0 μm, and a specific surface measured by BET of about 0.78 m²/g.

According to one embodiment, the micronized calcium silicate particles are characterized by a $d_{10}$ size ranging from more than 0.7 up to 1.7 μm, preferably from more than 0.7 to 1.0 μm, more preferably of about 0.8 μm. According to one embodiment, the micronized calcium silicate particles are characterized by a $d_{50}$ size ranging from more than 2.9 up to 8 μm, preferably from more than 3.0 to 5 μm, more preferably of about 3.4 μm. According to one embodiment, the micronized calcium silicate particles are characterized by a $d_{90}$ size ranging from more than 6.0 up to 20 μm, preferably from more than 6.0 to 10 μm, more preferably of about 7.2 μm. According to one embodiment, the micronized calcium silicate particles are characterized by a $d_{10}$ size of about 0.8 μm, a $d_{50}$ of about 3.4 μm and a $d_{90}$ of about 7.2 μm. According to one embodiment, the micronized calcium silicate particles are characterized by a $d_{10}$ size of 0.8 μm, a $d_{50}$ of 3.4 μm and a $d_{90}$ of 7.2 μm. According to one embodiment, the micronized calcium silicate particles are characterized by a specific surface measured by BET (Brunauer, Emmett and Teller technic) ranging from 0.8 to 3 m²/g, preferably from 0.8 to 2 m²/g, more preferably of about 1.56 m²/g. According to one embodiment, the micronized calcium silicate particles are characterized by a $d_{10}$ size of 0.8 μm, a $d_{50}$ of 3.4 μm and a $d_{90}$ of 7.2 μm, and a specific surface measured by BET of about 1.56 m²/g.

In one embodiment, the powder phase of the invention consists in UCS particles according to the invention.

In one embodiment, the powder phase of the invention comprises or consists in a mixture of UCS particles according to the invention and non-ultrafine calcium silicate particles, such as for example crushed, coarsely grinded and/or micronized calcium silicate particles.

In one embodiment, the powder phase of the invention comprises UCS particles according to the invention as source of calcium silicate.

In one embodiment, the powder phase of the invention comprises a mixture of UCS particles according to the invention and non-ultrafine calcium silicate particles, such as for example crushed, coarsely grinded and/or micronized calcium silicate particles.

According to one embodiment, the powder phase comprises the UCS particles in an amount ranging from 10% to 100% by weight of the total weight of the powder phase, preferably from 10% to 98%, preferably from 15% to 60%, more preferably from 20 to 55%.

According to one embodiment, the powder phase comprises the calcium silicate mixture in an amount ranging from 10% to 100%, by weight to the total weight of the powder phase; preferably from 40% to 100%, from 50% to 95%, from 50% to 85%. This amount of calcium silicate mixture corresponds to the total amount of calcium silicate present in the powder phase, whatever the particle size distribution.

According to one embodiment, the calcium silicate mixture comprises UCS particles according to the invention and optionally of non-ultrafine calcium silicate particles. According to one embodiment, the calcium silicate mixture comprises from 10% to 100% of UCS particles by weight to the total weight of the calcium silicate mixture; preferably from 10% to 100%, 10% to 70%, from 30% to 70%, from 30% to 60%, from 30% to 50%. In a specific embodiment, the amount of UCS particles is of about 50% by weight to the total weight of the calcium silicates present in the powder phase.

According to one embodiment, the powder phase comprises non-ultrafine calcium silicate particles in an amount ranging from 0% to 70% by weight of the total weight of the powder phase. In one embodiment, the powder phase does not comprise non-ultrafine calcium silicate particles. In another embodiment, the powder phase comprises non-ultrafine calcium silicate particles in an amount ranging from 10% to 60% preferably from 20% to 50%, more preferably from 25 to 45%.

According to one embodiment, the calcium silicate mixture present in the powder phase comprises:
- from 10% to 100% of ultrafine calcium silicate particles according to the invention; and
- from 0% to 90% of crushed, coarsely grinded and/or micronized calcium silicate particles, by weight to the total weight of the calcium silicate mixture.

According to one embodiment, the calcium silicate mixture comprises 50% of UCS particles, and 50% of coarsely grinded calcium silicate particles, by weight to the total weight of the calcium silicate mixture. According to one embodiment, the calcium silicate mixture comprises or consists of 50% of UCS particles, and 50% of crushed calcium silicate particles, by weight to the total weight of the calcium silicate mixture. According to one embodiment, the calcium silicate mixture comprises or consists of 50% of ultrafine tricalcium silicate (C3S), and 50% of coarsely grinded calcium silicate particles, by weight to the total weight of the calcium silicate mixture. According to one embodiment, the calcium silicate mixture comprises or consists of 50% of ultrafine tricalcium silicate particles (C3S), and 50% of crushed calcium silicate particles, by weight to the total weight of the calcium silicate mixture.

According to one embodiment, the calcium silicate mixture comprises or consists of 30% of UCS particles, and 70% of coarsely grinded calcium silicate particles, by weight to the total weight of the calcium silicate mixture. According to one embodiment, the calcium silicate mixture comprises or consists of 30% of UCS particles, and 70% of crushed calcium silicate particles, by weight to the total weight of the calcium silicate mixture. According to one embodiment, the calcium silicate mixture comprises or consists of 30% of ultrafine tricalcium silicate particles (C3S), and 70% of coarsely grinded calcium silicate particles, by weight to the total weight of the calcium silicate mixture. According to one embodiment, the calcium silicate mixture comprises or consists of 30% of ultrafine tricalcium silicate particles (C3S), and 70% of crushed calcium silicate particles, by weight to the total weight of the calcium silicate mixture.

According to one embodiment, the calcium silicate mixture comprises or consists of 70% of UCS particles, and 30% of coarsely grinded calcium silicate particles, by weight to the total weight of the calcium silicate mixture. According to one embodiment, the calcium silicate mixture comprises or consists of 70% of UCS particles, and 30% of crushed calcium silicate particles, by weight to the total weight of the calcium silicate mixture. According to one embodiment, the calcium silicate mixture comprises or consists of 70% of ultrafine tricalcium silicate particles (C3S), and 30% of coarsely grinded calcium silicate particles, by weight to the total weight of the calcium silicate mixture. According to one embodiment, the calcium silicate mixture comprises or consists of 70% of ultrafine tricalcium silicate particles (C3S), and 30% of crushed calcium silicate particles, by weight to the total weight of the calcium silicate mixture.

According to one embodiment, the calcium silicate mixture comprises or consists of 20% of UCS particles, and 80% of coarsely grinded calcium silicate particles, by weight to the total weight of the calcium silicate mixture. According to one embodiment, the calcium silicate mixture comprises or consists of 20% of UCS particles, and 80% of crushed calcium silicate particles, by weight to the total weight of the calcium silicate mixture. According to one embodiment, the calcium silicate mixture comprises or consists of 20% of ultrafine tricalcium silicate particles (C3S), and 80% of coarsely grinded calcium silicate particles, by weight to the total weight of the calcium silicate mixture. According to one embodiment, the calcium silicate mixture comprises or consists of 20% of ultrafine tricalcium silicate particles (C3S), and 80% of crushed calcium silicate particles, by weight to the total weight of the calcium silicate mixture.

According to one embodiment, the calcium silicate mixture does not comprise crushed calcium silicate particles. According to one embodiment, the calcium silicate mixture does not comprise crushed C3S particles.

According to one embodiment, the powder phase comprises a Portland cement and/or a mineral trioxide aggregate (MTA). According to one embodiment, the powder phase comprises a Portland cement and/or a mineral trioxide aggregate (MTA) in which the calcium silicate particles are ultrafine calcium silicate as defined in the present invention. According to one embodiment, the powder phase comprises a Portland cement and/or a mineral trioxide aggregate (MTA) that has (have) been grinded so that the calcium silicate particles comprised therein have the $d_{10}$, $d_{50}$, $d_{90}$ and $S_{sp\acute{e}}$ as defined for the UCS particles of the present invention. According to one embodiment, the calcium silicate mixture of the powder phase comprises or consists of calcium silicate present in a Portland cement and/or a mineral trioxide aggregate (MTA).

According to one embodiment, the powder phase further comprises additives such as for example radiopacifiers, setting accelerators, pigments, water reducing agents, texturing agents, pH stabilizing agents, surfactants, fillers, and mixtures thereof.

According to one embodiment, the radiopacifier is selected from zirconium oxide, bismuth oxide, cerium oxide, barium sulphate, calcium tungstate, titanate dioxide, ytterbium oxide and mixtures thereof. In a specific embodiment, the radiopacifier is zirconium oxide. According to one embodiment, the setting accelerator is calcium carbonate, calcium oxide, calcium phosphate, sodium bicarbonate, calcium lactate, calcium chloride or mixtures thereof. According to one embodiment, the setting accelerator is calcium carbonate, calcium oxide or mixtures thereof. According to one embodiment, the setting accelerator is calcium chloride. According to one embodiment, the pigments may be iron oxides. According to one embodiment, the water-reducing agent is selected from glenium, polynaphtalene sulfonate, modified polycarboxylate. According to one embodiment, the texturing agents may be for example selected from silica, povidone (also named polyvinylpyrrolidone), cellulose or derivatives thereof such as methylcellulose, hydroxypropylcellulose and hydroxyethylcellulose, polymers such as acrylamide/sodium acryloyldimethyltaurate copolymer isohexadecane and hydroxyethyl acrylate/sodium acryloyl dimethyl taurate copolymer, mineral fillers, fumed silica (hydrophilic and/or hydrophobic), xanthan gum, or mixtures thereof. According to one embodiment, the pH stabilizing agent is a mineral acid or an organic acid. According to one embodiment, the surfactant is a polysorbate.

According to one embodiment, the powder phase comprises at least one additive, wherein the additive is preferably selected from radiopacifiers, setting accelerators, pigments, and texturing agents. According to one embodiment, the powder phase comprises one or more additives selected from radiopacifiers (such as zirconium oxide, bismuth oxide, cerium oxide, barium sulphate, calcium tungstate, titanate dioxide, ytterbium oxide or mixtures thereof), setting accelerators (such as calcium carbonate, calcium oxide, calcium phosphate or mixture thereof), pigments (such as iron oxides) and mixtures thereof. According to one embodiment, the powder phase comprises at least one additive in an amount ranging from 0% to 60% in weight to the total weight of the powder phase; preferably from 2% to 50%; more preferably from 2% to 35%.

According to one embodiment, the powder phase comprises at least one radiopacifier, such as for example zirconium oxide, bismuth oxide, cerium oxide, barium sulphate, calcium tungstate, titanate dioxide, ytterbium oxide and mixtures thereof. In a specific embodiment, the powder phase comprises zirconium oxide.

According to one embodiment, the powder phase comprises from 0 to 40% of radiopacifier in weight to the total weight of said powder phase; preferably from 2 to 35%, from 5 to 35%, preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or 35%.

According to one embodiment, the powder phase comprises at least one setting accelerator, such as for example calcium carbonate, calcium oxide, calcium phosphate and mixtures thereof. In a specific embodiment, the powder phase comprises calcium carbonate. In a specific embodiment, the powder phase comprises calcium carbonate and calcium oxide.

According to one embodiment, the powder phase comprises a setting accelerator, preferably calcium carbonate, and the ratio between the $d_{50}$ size of the UCS particles and the $d_{50}$ size of the setting accelerator particles is less than 10, preferably is ranging from 0.1 to 9, preferably from 0.2 to 5, more preferably from 0.5 to 2.

According to one embodiment, the powder phase comprises from 0 to 25% of setting accelerator in weight to the total weight of said powder phase; preferably from 4 to 20%, preferably from 4 to 15%, preferably 1, 2, 3, 4, 5, 6, 7, 8, 9, 10, 11, 12, 13, 14, 15, 16, 17, 18, 19 or 20%.

According to one embodiment, the powder phase comprises at least one pigment or a mixture of pigments such as iron oxides. One skilled in the art is able to select suitable mixtures of pigments so that the composition has the expected color.

According to one embodiment, the powder phase comprises from 15% to 98% in weight of the total weight of the powder phase of ultrafine particles of calcium silicate having a $d_{50}$ size ranging from 0.7 μm to 2.9 μm and a $d_{90}$ size ranging from 1.4 μm to 6.0 μm, wherein the $d_{50}$ and $d_{90}$ sizes are measured by laser diffraction;

from 2% to 35% in weight of the total weight of the powder phase of a radiopacifier; and optionally one or more additive selected from setting accelerators, pigments, water reducing agents, texturing agents, pH stabilizing agents, surfactants, and fillers.

According to one embodiment, the powder phase comprises from 15% to 98% in weight of the total weight of the powder phase of ultrafine particles of calcium silicate having a $d_{50}$ size ranging from 1 μm to 2.1 μm and a $d_{90}$ size ranging from 2 μm to 5.0 μm, wherein the $d_{50}$ and $d_{90}$ sizes are measured by laser diffraction;

from 2% to 35% in weight of the total weight of the powder phase of a radiopacifier; and optionally one or more additive selected from setting accelerators, pigments, water reducing agents, texturing agents, pH stabilizing agents, surfactants, and fillers.

According to one embodiment, the powder phase comprises from 15% to 98% in weight of the total weight of the powder phase of ultrafine particles of calcium silicate having a $d_{10}$ size ranging from 0.5 μm to 0.9 μm, preferably from 0.5 μm to 0.82 μm or from 0.5μ to 0.8 μm, even more preferably from 0.5 μm to 0.7 μm; a $d_{50}$ size ranging from 0.7 μm to 2.9 μm, preferably ranging from 0.8 μm to 2.5 μm, preferably ranging from 1 μm to 2.1 μm; and a $d_{90}$ size ranging from 1.3 μm to 7.0 μm, preferably ranging from 1.5 μm to 7 μm or ranging from 2 μm to 5 μm; wherein the $d_{10}$, $d_{50}$ and $d_{90}$ sizes are measured by laser diffraction.

from 2% to 35% in weight of the total weight of the powder phase of a radiopacifier; and optionally one or more additive selected from setting accelerators, pigments, water reducing agents, texturing agents, pH stabilizing agents, surfactants, and fillers.

According to one embodiment, the powder phase comprises from 15% to 98% in weight of the total weight of the powder phase of ultrafine particles of tricalcium silicate (C3S) having a $d_{50}$ size ranging from 0.7 μm to 2.9 μm, preferably a $d_{50}$ size ranging from 1 μm to 2.1 μm, and a $d_{90}$ size ranging from 1.4 μm to 6.0 μm, preferably a $d_{90}$ size ranging from 2 μm to 5 μm, wherein the $d_{50}$ and $d_{90}$ sizes are measured by laser diffraction;

from 2% to 35% in weight of the total weight of the powder phase of a radiopacifier, preferably zirconium oxide; and optionally one or more additive selected from setting accelerators, pigments, water reducing agents, texturing agents, pH stabilizing agents, surfactants, and fillers.

According to one embodiment, the powder phase comprises from 15% to 98% in weight of the total weight of the powder phase of ultrafine particles of calcium silicate having;

a specific area, measured by BET technique, ranging from 3 to 11 m2/g;

a $d_{10}$ size of less than 0.7 m;

a $d_{50}$ size ranging from 0.7 $\mu$m to 2.9 $\mu$m; and a $d_{90}$ size ranging from 1.4 $\mu$m to 6.0 $\mu$m;

wherein the $d_{10}$, $d_{50}$ and $d_{90}$ sizes are measured by laser diffraction;

from 2% to 35% in weight of the total weight of the powder phase of a radiopacifier, preferably zirconium oxide; and optionally one or more additive selected from setting accelerators, pigments, water reducing agents, texturing agents, pH stabilizing agents, surfactants, and fillers.

According to one embodiment, the powder phase comprises from 15% to 98% in weight of the total weight of the powder phase of ultrafine particles of calcium silicate having;

a specific area, measured by BET technique, ranging from 3 to 11 m2/g;

a $d_{10}$ size ranging from 0.5 $\mu$m to 0.9 $\mu$m;

a $d_{50}$ size ranging from 1 $\mu$m to 2.1 $\mu$m; and a $d_{90}$ size ranging from 2 $\mu$m to 5 $\mu$m;

wherein the $d_{10}$, $d_{50}$ and $d_{90}$ sizes are measured by laser diffraction;

from 2% to 35% in weight of the total weight of the powder phase of a radiopacifier, preferably zirconium oxide; and optionally one or more additive selected from setting accelerators, pigments, water reducing agents, texturing agents, pH stabilizing agents, surfactants, and fillers.

According to one embodiment, the powder phase comprises from 20% to 60% in weight of the total weight of the powder phase of ultrafine particles of tricalcium silicate having:

a specific area, measured by BET technique, ranging from 3 to 11 m²/g;

a $d_{10}$ size of less than 0.7 $\mu$m, preferably a $d_{10}$ size ranging from 0.5 $\mu$m to 0.9 $\mu$m;

a $d_{50}$ size ranging from 0.7 $\mu$m to 2.9 $\mu$m, preferably a $d_{50}$ size ranging from 1 $\mu$m to 2.1 $\mu$m; and a $d_{90}$ size ranging from 1.4 $\mu$m to 6.0 $\mu$m, preferably a $d_{90}$ size ranging from 2 $\mu$m to 5 $\mu$m;

wherein the $d_{10}$, $d_{50}$ and $d_{90}$ sizes are measured by laser diffraction;

from 0% to 50% in weight of the total weight of the powder phase of non-ultrafine particles of calcium silicate;

from 2% to 35% in weight of the total weight of the powder phase of a radiopacifier;

from 0% to 25% in weight of the total weight of the powder phase of one or more setting accelerator such as calcium carbonate, calcium oxide and mixture thereof.

According to one embodiment, the powder phase comprises from 20% to 60% in weight of the total weight of the powder phase of ultrafine particles of tricalcium silicate having:

a specific area, measured by BET technique, ranging from 3 to 11 m²/g;

a $d_{10}$ size ranging from 0.5 $\mu$m to 0.9 $\mu$m, preferably from 0.5 $\mu$m to 0.82 $\mu$m, even more preferably from 0.5 $\mu$m to 0.7 $\mu$m;

a $d_{50}$ size ranging from 0.7 $\mu$m to 2.9 $\mu$m, preferably ranging from 0.8 $\mu$m to 2.5 $\mu$m, preferably ranging from 1 $\mu$m to 2.1 $\mu$m; and a $d_{90}$ size ranging from 1.3 $\mu$m to 7.0 $\mu$m, preferably ranging from 1.5 $\mu$m to 7 $\mu$m or ranging from 2 $\mu$m to 5 $\mu$m; wherein the $d_{10}$, $d_{50}$ and $d_{90}$ sizes are measured by laser diffraction;

from 0% to 50% in weight of the total weight of the powder phase of non-ultrafine particles of calcium silicate;

from 2% to 35% in weight of the total weight of the powder phase of a radiopacifier;

from 0% to 25% in weight of the total weight of the powder phase of one or more setting accelerator such as calcium carbonate, calcium oxide and mixture thereof.

Liquid Phase

As mentioned above, dental restoration material of the invention may result from the mixture of the calcium silicate powder phase described above with an aqueous liquid phase.

According to one embodiment, the aqueous liquid phase comprises water, preferably purified water.

According to one embodiment, the aqueous liquid phase consists in water. In another embodiment, the aqueous liquid phase is an aqueous solution According to one embodiment, the aqueous liquid phase comprises from 10 to 100% of water, in weight to the total weight of said aqueous liquid phase, preferably from 20% to 90%, preferably from 30% to 90%, preferably from 35% to 85%. According to one embodiment, the liquid phase comprises from 50% to 90% of water in weight to the total weight of said liquid phase, preferably from 60% to 90%, more preferably from 60% to 85%, more preferably from 65% to 85%.

According to one embodiment, the aqueous liquid phase further comprises additives such as for example setting accelerators, water reducing agents, texturing agents, pH stabilizing agents, surfactants, fillers, and mixtures thereof. Examples of such additives are provided above with regards to the powder phase, and also apply for the additives of the liquid phase.

According to one embodiment, the aqueous liquid phase comprises at least one additive, wherein the additive is preferably selected from setting accelerators and water reducing agents. According to one embodiment, the aqueous liquid phase comprises one or more additives selected from setting accelerators (such as calcium chloride), water reducing agents (such as modified polycarboxylate, glenium, polynaphtalenesulfonate or mixtures thereof) and mixtures thereof.

According to one embodiment, the liquid phase comprises at least one additive in an amount ranging from 0% to 40% in weight to the total weight of the liquid phase; preferably from 10% to 35%; more preferably from 15% to 35%.

According to one embodiment, the liquid phase comprises at least one setting accelerator; preferably calcium chloride. According to one embodiment, the liquid phase comprises or consists of water and calcium chloride. According to one embodiment, the liquid phase comprises from 1% to 40% of calcium chloride, in weight of the total weight of the liquid phase; preferably from 5% to 35%. In a specific embodiment, the liquid phase comprises from 15% to 35% of calcium chloride, in weight of the total weight of the liquid phase; preferably from 20% to 30%. In another embodiment, the liquid phase does not comprise a setting accelerator, especially the liquid phase does not comprise calcium chloride.

According to one embodiment, the liquid phase comprises at least one water reducing agent, such as for example glenium, polynaphtalene sulfonate or modified polycarboxylates. According to one embodiment, the liquid phase comprises or consists of water and a water reducing agent (preferably a modified polycarboxylate). According to one embodiment, the liquid phase comprises from 0% to 40% of water reducing agent, in weight of the total weight of the liquid phase; preferably from 0.5% to 35%. In a specific embodiment, the liquid phase comprises from 0% to 5% of water reducing agent, in weight of the total weight of the liquid phase; preferably from 0% to 2%.

According to one embodiment, the liquid phase comprises at least one setting accelerator and at least one water reducing agent. According to one embodiment, the liquid phase consists or comprises water, a setting accelerator and a water reducing agent; preferably the liquid phase consists or comprises water, calcium chloride and a modified polycarboxylate.

According to one embodiment, the aqueous liquid phase comprises:

from 60% to 85% in weight of the total weight of the aqueous liquid phase of water;

from 5% to 35% in weight of the total weight of the aqueous liquid phase of setting accelerator, preferably calcium chloride; and from 0% to 5% in weight of the total weight of the aqueous liquid phase of reducing agent, preferably a modified polycarboxylate.

According to one embodiment, the aqueous liquid phase further comprises a non-aqueous liquid. In one embodiment, the non-aqueous liquid is selected from glycerol, glycols, silicones or mixture thereof; preferably the non-aqueous liquid is a glycol such as propylene glycol or polyethylene glycol. According to one embodiment, the glycol compound is selected from ethylene glycol, propylene glycol (or propane-1,2-diol), trimethylene glycol (or propane-1,3-diol), butylene glycol (or butane-1,3-diol), butane-1,2-diol, butane-1,4-diol, pentylene glycol (or pentane-1,5-diol), pentane-1,2-diol, pentane-1,3-diol, pentane-1,4-diol dipropylene glycol or polyethylene glycol; preferably the glycol compound is ethylene glycol, propylene glycol, dipropylene glycol or polyethylene glycol. According to one embodiment, the polyethylene glycol has an average molecular mass M ranging from 100 g/mol to 10 000 g/mol, preferably from 200 g/mol to 5 000 g/mol; more preferably is about 300 g/mol or about 4 000 g/mol. According to one embodiment, the silicone is selected from alkylsilicones, more preferably is selected from methicone, dimethylmethicone, caprylylmethicone or their copolymers or mixtures thereof. According to one embodiment, the silicone is selected from methicone, dimethylmethicone and caprylylmethicone.

According to one embodiment, in the liquid phase, the mass ratio of water to non-aqueous liquid is ranging from 50/50 to 80/20. According to one embodiment, the liquid phase comprises of a mixture 50% wt. of water/50% wt. of a non-aqueous liquid. According to one embodiment, the liquid phase comprises of a mixture 70% of water/30% of a non-aqueous liquid. According to one embodiment, the liquid phase comprises of a mixture 80% of water/20% of a non-aqueous liquid. According to one embodiment, the mixture water/non-aqueous liquid in the liquid phase, comprises at least 10%, 20%, 30%, 40%, 50%, 60%, 70%, 80%, 90% of water. According to one embodiment, the liquid phase comprises from 10 to 100% of a mixture of water and non-aqueous liquid in weight to the total weight of said liquid phase; preferably from 50 to 90%, preferably from 65 to 85%, preferably from 65 to 75%. According to one embodiment, the aqueous liquid phase comprises from 0 to 50% of non-aqueous liquid in weight to the total weight of said liquid phase; preferably from 0 to 45%, preferably from 10 to 45%, preferably from 10 to 20%.

According to another embodiment, the liquid phase consists or comprises water, a non-aqueous liquid, a setting accelerator and a water reducing agent; preferably the liquid phase consists or comprises (i) water, ethylene glycol, calcium chloride and a modified polycarboxylate; or (ii) water, polyethylene glycol, calcium chloride and a modified polycarboxylate.

According to one embodiment, the liquid phase comprises:

from 35% to 85% of water, from 0 to 45% of non-aqueous liquid, from 5% to 35% of a setting accelerator, from 0% to 35% of other additives, such as water reducing agents; by weight to the total weight of the liquid phase.

Kit

The present invention also relates to a kit suitable to produce the dental restoration material of the invention, the kit comprising a powder phase comprising UCS particles and an aqueous liquid phase as those described above.

In one embodiment, the kit of the invention comprises a first container and a second container. In one embodiment, the first container contains a solid phase, preferably powder phase, more preferably a powder phase comprising UCS particles, more preferably a powder phase comprising UCS particles as described above. In one embodiment, the second container contains a liquid phase, preferably an aqueous liquid phase, more preferably an aqueous liquid phase as described above.

According to one embodiment, the kit of the invention thus comprises:

a first container containing a solid phase, preferably a powder phase, comprising UCS particles as defined above; and a second container containing a liquid phase, preferably an aqueous liquid phase, more preferably an aqueous liquid phase as described above.

All above embodiments relative to the powder phase and to the aqueous liquid phase also apply to the powder phase and to the liquid phase present in the kit of the invention. Specific embodiments are further detailed below.

According to one embodiment, the invention provides a kit for producing a dental restoration material, said kit comprising:

a first container containing a powder phase comprising:

from 15% to 98% in weight of the total weight of the powder phase of ultrafine particles of calcium silicate having a $d_{50}$ size ranging from 0.7 μm to 2.9 μm, preferably from 0.8 μm to 2.5 μm, even more preferably from 0.8 µm to 2.1 µm, and a $d_{90}$ size ranging from 1.3 µm to 7.0 µm, preferably from 1.4 µm to 7 µm, from 1.4 µm to 6 µm or from 2 µm to 5 µm, wherein the $d_{50}$ and $d_{90}$ sizes are measured by laser diffraction;

from 2% to 35% in weight of the total weight of the powder phase of a radiopacifier; and optionally one or more additive selected from setting accelerators, pigments, water reducing agents, texturing agents, pH stabilizing agents, surfactants, and fillers; and a second container containing an aqueous liquid phase;

and wherein the weight ratio of the powder phase present in the kit to the liquid phase present in the kit ranges from 1.9 to 5.5; preferably from 2 to 5; preferably from 2.5 to 4.0.

According to one embodiment, the calcium silicate present in the powder phase of the kit is selected from tricalcium silicate (C3S), dicalcium silicate (C2S) and any combinations thereof; preferably the calcium silicate is tricalcium silicate.

According to one embodiment, the powder phase of the kit comprises a Portland cement and/or mineral trioxide aggregates (MTA).

According to one embodiment, the powder phase of the kit further comprises non-ultrafine particles of calcium silicate.

According to one embodiment, the amount of ultrafine calcium silicate particles presents in the powder phase of the kit ranges from 10% to 100% by weight to the total weight of calcium silicate present in the powder phase; preferably ranges from 10% wt to 70% wt; more preferably from 10% wt to 50% wt.

According to one embodiment, the radiopacifier present in the powder phase of the kit is selected from zirconium oxide, bismuth oxide, cerium oxide, barium sulphate, calcium tungstate, titanate dioxide, ytterbium oxide and mixtures thereof; preferably the radiopacifier is zirconium oxide.

According to one embodiment, the powder phase of the kit comprises one or more additive, wherein the additive is selected from setting accelerators, such as calcium carbonate, calcium oxide, calcium phosphate and mixture thereof; and pigments, such as iron oxides.

According to one embodiment, the powder phase of the kit comprises:

from 20% to 60% in weight of the total weight of the powder phase of ultrafine particles of tricalcium silicate having:

a specific area, measured by BET technique, ranging from 3 to 11 m²/g;

a $d_{10}$ size less than 0.7 µm;

a $d_{50}$ size ranging from 0.7 µm to 2.9 µm; and a $d_{90}$ size ranging from 1.4 µm to 6.0 µm;

wherein the $d_{10}$, $d_{50}$ and $d_{90}$ sizes are measured by laser diffraction;

from 0% to 50% in weight of the total weight of the powder phase of non-ultrafine particles of calcium silicate;

from 2% to 35% in weight of the total weight of the powder phase of a radiopacifier; and from 0% to 25% in weight of the total weight of the powder phase of one or more setting accelerator selected from calcium carbonate, calcium oxide and mixture thereof.

According to one embodiment, the powder phase of the kit comprises:

from 20% to 60% in weight of the total weight of the powder phase of ultrafine particles of tricalcium silicate having:

a specific area, measured by BET technique, ranging from 3 to 11 m²/g;

a $d_{10}$ size ranging from 0.5 µm to 0.9 µm, preferably from 0.5 µm to 0.82 µm;

a $d_{50}$ size ranging from 0.7 µm to 2.9 µm, preferably ranging from 1 µm to 2.1 µm; and a $d_{90}$ size ranging from 1.4 µm to 6.0 µm, preferably from 2 µm to 5 µm;

wherein the $d_{10}$, $d_{50}$ and $d_{90}$ sizes are measured by laser diffraction;

from 0% to 50% in weight of the total weight of the powder phase of non-ultrafine particles of calcium silicate;

from 2% to 35% in weight of the total weight of the powder phase of a radiopacifier; and from 0% to 25% in weight of the total weight of the powder phase of one or more setting accelerator selected from calcium carbonate, calcium oxide and mixture thereof.

According to one embodiment, the aqueous liquid phase present in the kit is water.

According to one embodiment, the aqueous liquid phase present in the kit further comprises one or more additive, wherein the additive is selected from setting accelerators, such as calcium chloride; and water reducing agents, such as a modified polycarboxylate.

According to one embodiment, the aqueous liquid phase present in the kit comprises:

from 60% to 85% in weight of the total weight of the aqueous liquid phase of water;

from 5% to 35% in weight of the total weight of the aqueous liquid phase of setting accelerator, preferably calcium chloride; and from 0% to 5% in weight of the total weight of the aqueous liquid phase of reducing agent, preferably a modified polycarboxylate.

Mixed Composition

According to one embodiment, the restorative material of the invention results from the hardening of a composition obtained by mixing the powder phase and the aqueous liquid phase described.

According to one embodiment, the composition resulting from the mixture of the powder and aqueous liquid phases as defined above, is creamy (i.e. is a paste in which the components are homogenously mixed together, without any aggregates). According to one embodiment, the creamy texture may be determined by visual observation. According to one embodiment, the composition of the invention is colored, preferably white.

According to one embodiment, the composition of the invention does not comprise any aluminate, such as calcium aluminate. According to one embodiment, the composition of the invention does not comprise any halogen or halogenated compounds, such as for example fluoride. According to one embodiment, the composition of the invention does not comprise any phosphates such as for example calcium phosphate. According to one embodiment, the composition of the invention does not comprise any porous compounds. According to one embodiment, the composition of the invention does not comprise any porous fillers and/or porous fibers.

According to one embodiment, the weight ratio between the powder phase and the aqueous liquid phase ranges from 1.9 to 5.5, preferably from 2 to 5, preferably from 2.5 to 4.0. The weight ratio between the powder phase and the aqueous liquid phase is adapted so that a suitable creamy aspect is obtained for the resulting composition. The weight ratio between the powder phase and the aqueous liquid phase also enable to control the compressive strength of the hardened restorative material. According to one embodiment, the weight ratio between the powder phase and the aqueous liquid phase ranges from 2.4 to 4.0; preferably is 2.4, 2.5, 2.6, 2.7, 2.8, 2.9, 3.0, 3.1, 3.2, 3.3, 3.4, 3.5, 3.6, 3.7, 3.8, 3.9, 4.0.

According to one embodiment, the setting time of the composition resulting from the mixture of the powder and aqueous liquid phases ranges from more than 0 min to 1 h; preferably from 1 min to less than 15 min; more preferably from 1 min to less than 12 min; more preferably from 1 min to less than 9 min; more preferably from 1 min to less than 8 min; even more preferably from 1 min to less than 7 min. According to one embodiment, the setting time of the composition of the invention ranges from 1 min to 12 min, preferably from 4 min to 9 min.

According to one embodiment, the working time of the composition resulting from the mixture of the powder and aqueous liquid phases ranges from more than 0 min to 10 min; preferably from 1 min to less than 5 min; more preferably from 1 min to 3 min.

According to one embodiment, the composition results from the mixture of a powder phase which comprises or consists of a calcium silicate mixture comprising from 10% to 100% of ultrafine tricalcium silicate particles and from 0% to 90% of micronized, coarsely grinded or crushed calcium silicate particles, preferably from 10% to 60% of ultrafine tricalcium silicate particles and from 40% to 90% of micronized, coarsely grinded or crushed calcium silicate particles; with an aqueous liquid phase comprising water and calcium chloride. According to one embodiment, the composition of the invention resulting from the mixture of a powder phase comprising a calcium silicate mixture comprising from 10% to 100% of ultrafine tricalcium silicate particles and from 0% to 90% of micronized, coarsely grinded or crushed calcium silicate particles, preferably from 10% to 60% of ultrafine tricalcium silicate particles and from 40% to 90% of micronized, coarsely grinded or crushed calcium silicate particles; with an aqueous liquid phase comprising water and calcium chloride, has a setting time from more than 0 min to 12 min, preferably from 1 min to 9 min, more preferably from 1 min to less than 8 min; even more preferably from 1 min to less than 7 min.

Premixed Water-Free Composition

The invention also provides a premixed water-free composition as starting composition enabling to produce the dental restoration material of the invention. In one embodiment, the invention thus provides a premixed water-free calcium silicate composition comprising UCS particles.

In one embodiment, the premixed water-free composition results from the mixture of:
- a powder phase as defined above comprising ultrafine calcium silicate particles, wherein the powder phase is anhydrous; and
- a water-free liquid phase, comprising a non-aqueous liquid and being free of water.

The water-free premixed paste can be directly used for dental restoration and thus in situ hardens when placed in the oral cavity of the patient by contact with physiological liquids, thereby providing the hardened material. Alternatively, the water-free premixed paste can afterwards be mixed with an aqueous liquid phase or an aqueous paste. In such case, the mixture of the premixed water-free calcium silicate paste with an aqueous phase (either under the form of a liquid or of a paste) provokes the hardening of the composition and provides a hardened material. In one embodiment, the aqueous phase to be mixed with the water-free premixed paste comprises water and optionally additives such as for example setting accelerators or water-reducing agents.

All above embodiments relative to the powder phase also apply to the powder present in the premixed water-free composition.

According one embodiment, the non-aqueous liquid is selected from glycerol, glycols, silicones or mixture thereof;

According to one embodiment, glycols are selected from ethylene glycol, propylene glycol (or propane-1,2-diol), trimethylene glycol (or propane-1,3-diol), butylene glycol (or butane-1,3-diol), butane-1,2-diol, butane-1,4-diol, pentylene glycol (or pentane-1,5-diol), pentane-1,2-diol, pentane-1,3-diol, pentane-1,4-diol dipropylene glycol or polyethylene glycol; preferably the glycol compound is ethylene glycol, propylene glycol, dipropylene glycol or polyethylene glycol. According to one embodiment, the polyethylene glycol has an average molecular mass M ranging from 100 g/mol to 10 000 g/mol, preferably from 200 g/mol to 5 000 g/mol; more preferably is about 300 g/mol or about 4 000 g/mol. Preferably the non-aqueous liquid is a glycol such as for example propylene glycol or polyethylene glycol.

According to one embodiment, the silicones are selected from alkylsilicones, more preferably from methicone, dimethylmethicone, caprylylmethicone or their copolymers or mixtures thereof. According to one embodiment, the silicone is selected from methicone, dimethylmethicone and caprylylmethicone.

According to one embodiment, the water-free premixed paste comprises from 10 to 50%, preferably from 20 to 50%, preferably from 30 to 50%, preferably from 40 to 50%, preferably 10, 15, 20, 25, 30, 35, 40, 45 or 50%, of non-aqueous liquid in weight to the total weight of said paste. According to one embodiment, the water-free premixed paste comprises 20; 21; 22; 23; 24; 25; 26; 27; 28; 29; 30; 31; 32; 33, 34, 35; 36; 37; 38; 39; 40; 41; 42; 43; 44; 45; 46; 47; 48; 49 or 50% of non-aqueous liquid in weight to the total weight of said paste.

Hardened Calcium Silicate-Based Restorative Material

This invention also relates to a hardened restorative material, preferably a dental restorative material obtainable by the hydraulic setting of a composition comprising ultrafine calcium silicate particles as defined above. Hardening occurs by hydration of the calcium silicate present in the composition. The composition may be a composition resulting from the mixture of a powder phase comprising ultrafine calcium silicate particles and an aqueous liquid phase, as described above; or alternatively a premixed water-free composition as described above.

According to one embodiment, the hardened restorative material has a compressive strength of more than 10 MPa, preferably of more than 50 MPa, more than 100 MPa, more than 120 MPa, more than 130 MPa, more than 140 MPa, even more preferably of more than 150 MPa. Preferably compressive strength is measured using a compression bench apparatus, preferably applying a force of 10 kN. According to one embodiment, the hardened restorative material has a compressive strength at 24 hours, of more than 10 MPa, preferably of more than 50 MPa, more than 100 MPa, more than 120 MPa, more than 130 MPa, more than 140 MPa, even more preferably of more than 150 MPa. According to one embodiment, the hardened restorative material has a compressive strength ranging from 160 MPa to 260 MPa. According to one embodiment, the hardened restorative material has a compressive strength is about 161 MPa, 174 MPa, 175 MPa, 181 MPa, 194 MPa, 243 MPa or 250 MPa.

According to one embodiment, the hardened restorative material has a radioopacity ranging from 1 to 15 mm, preferably from 3 to 10 mm, preferably from 4 to 9.5 mm Aluminum. In the present invention, the radioopacity of the hardened material fulfils the standardization of dental materials, especially the specification NF EN ISO 6876.

Use

According to one embodiment, the compositions and kits of the invention may be used in the dental field. According to one embodiment, the compositions and kits of the invention may also be used in orthopedics, in bone restoration, in craniofacial and/or maxillofacial surgery.

In one embodiment, the compositions and kits of the invention may be used to provide a material for treating the crown of a tooth, for example temporary enamel restoration, permanent dentin restoration, deep or large carious lesions restoration, deep cervical or radicular lesions restoration, pulp capping or pulpotomy.

In one embodiment, the compositions and kits of the invention may also be used to provide a material for treating the root of a tooth, such as for example root and furcation perforations, internal/external resorptions, apexification or retrograde surgical filling.

In one embodiment, the invention relates to the use of the compositions and kits of the invention for treating the crown of a tooth, for example temporary enamel restoration, permanent dentin restoration, deep or large carious lesions restoration, deep cervical or radicular lesions restoration, pulp capping or pulpotomy; and/or the root of a tooth, such as for example root and furcation perforations, internal/external resorptions, apexification or retrograde surgical filling. In one embodiment, the invention relates to a method for treating the crown of a tooth, for example temporary enamel restoration, permanent dentin restoration, deep or large carious lesions restoration, deep cervical or radicular lesions restoration, pulp capping or pulpotomy; and/or the root of a tooth, such as for example root and furcation perforations, internal/external resorptions, apexification or retrograde surgical filling; in a subject in need thereof, comprising the use the compositions and kits of the invention.

According to one embodiment, the compositions and kits of the invention may be used in treating a bone and/or dental disorder or disease in a subject in need thereof. According to one embodiment, the present invention refers to the use of the compositions and kits of the invention for treating a bone and/or dental disorder or disease in a subject in need thereof. According to one embodiment, the present invention refers to a method for treating a bone and/or dental disorder or disease in a subject in need thereof by using the compositions and kits of the invention.

According to one embodiment, the compositions and kits of the invention may be used in bone restoration or bone regeneration. According to one embodiment, the present invention refers to the use of the compositions and kits of the invention for bone restoration or bone regeneration. According to one embodiment, the present invention refers to a method for bone restoration or bone regeneration by using the compositions and kits of the invention.

Medical Device

The invention also relates to a medical device containing a composition comprising ultrafine calcium silicate particles as defined above.

In one embodiment, the medical device is an injection system, preferably a syringe, comprising a composition obtained by the mixing of the powder phase and the aqueous liquid phase described above. In one embodiment, the medical device is an injection system, preferably a syringe, comprising the kit powder-liquid described above.

In another embodiment, the medical device is an injection system, preferably a syringe, comprising the premixed water-free composition described above. In a specific embodiment, the syringe is a dual syringe, one compartment comprising the premixed water-free composition described above and the second compartment comprising an aqueous phase.

EXAMPLES

The present invention is further illustrated by the following examples.

Abbreviations

C3S: tricalcium silicate;
CS: calcium silicate;
g: gram(s);
MTA: mineral trioxide aggregate;
$m^2/g$: square meter per gram;
min: minute(s);
mL: milliliter(s);
mm: millimeter(s);
μm: micrometer(s);
ratio p/l: mass ratio of the powder phase on the liquid phase;
rpm: road per minute;
UCS: ultrafine calcium silicate
UTCS: ultrafine tricalcium silicate (tricalcium silicate particles consisting of 100% of ultrafine C3S particles).

Materials and Methods

Microscopy

The morphology of calcium silicate particles such as C3S particles was observed with the Keyence® microscope before and after the grinding process. To avoid agglomerates during the analysis, the sample to be analyzed was placed on a glass slide with a drop of ethanol.

Size Distribution

The size distribution the ultrafine calcium silicate particles such as C3S particles, was determined using a Malvern® particle size analyzer based on laser diffraction particle sizing technique. A sample of the powder to be analyzed was dispersed in ethanol and sonicated to separate powder aggregates. A few drops of the suspension are then introduced in the tank of the particle sized analyzer in order to have between 2% and 10% of filling of the measuring cell. The tank is stirred at about 2000 rpm Specific Area: BET Technique Specific area analyzes were performed by nitrogen adsorption sorptometry with the GEMINI VII Micromeritics® apparatus. The analyzes were done with 1 g of powder. The samples were previously degassed for 3 hours at 250° C. before analysis by nitrogen adsorption.

Setting Time

Setting time measurements were performed using a Gillmore apparatus. The material to be tested is placed into molds 10 mm in diameter and 2 mm thick and then placed in a water bath at 37° C. The setting of the material is assessed using a Gillmore needle of 400 g. The material is considered as being set when the needle leaves no trace on the surface of the mold. The setting time corresponds to the period of time between the placement of the molds into the water bath and the observed setting.

Compressive Strength

Compressive strength measurements were performed using a compression bench apparatus, from MTS. The cement is slowly introduced into a mold 6 mm high/4 mm in diameter, checking that there are no bubbles. The molds are placed in the water bath at 37° C. for 15 min. The samples are then demolded and placed in a test tube containing purified water and left in the water bath for 24 hours. After 24 h the samples are polished on each side and compressed using a MTS compression bench applying a force of 10 kN.

Part I: Preparation of Ultrafine Tricalcium Silicate Particles

Particles of C3S having a coarse particle size were grinded in order to obtain ultrafine C3S particles having the following characteristics:

- a specific area ranging from 3 to 11 $m^2/g$;
- a $d_{10}$ size ranging from 0.4 µm to 0.82 µm, preferably 0.4 µm to 0.8 µm;
- a $d_{50}$ size ranging from 0.8 µm to 2.1 µm;
- a $d_{90}$ size ranging from 1.4 µm to 7.0 µm.

Depending on the apparatus, distinct processes are carried out that are exemplified, but are not limited, herein below.

Example 1: Process for Manufacturing Ultrafine Tricalcium Silicate (UTCS) Particles by Mechanical Grinding The preparation of UTCS particles has been implemented via the general procedure herein below, with the apparatus EMAX® of RETSCH.

Material

The crushed C3S particles used in the examples below were obtained by crushing crude C3S with a Retch crusher. The coarsely grinded C3S particles used in the examples below were obtained by further crushing the crushed C3S particles with a grinding roller (Crusher Faure)

General Procedure

In a first step, crushed or coarsely grinded C3S particles mixed with isopropanol, are added in the grinding chamber of the apparatus. Then, grinding beads are added to the previous mixture. In the process of the invention, grinding beads may be for example, zirconium oxide beads with a diameter ranging from 0.4 mm to 0.8 mm. Secondly, grinding is carried out for 20 to 30 min. According to the present invention, grinding may be carried out on a longer time period until achieving ultrafine particles having particle sizes as defined above. Finally, the grinded mixture is dried and isopropanol is removed. After being sifted, ultrafine powder of C3S particles is obtained.

Whatever the apparatus used, the process of the invention requires that grind beads and grinding chamber are not made of stainless steel. Preferably, the process comprises the use of grind beads and grinding chamber made of and/or coated with zirconium oxide, tungsten carbide and/or silicon carbide.

Example 1a: The general procedure was carried out with 45 g of coarsely grinded C3S particles, 30 mL of isopropanol and 90 g of grinding beads. Grinding with the apparatus EMAX® was carried out with a grinding rate of about 1900 rpm for 20 min. Drying was implemented at about 50° C.

Part II: Characterization of Ultrafine C3S Particles

Example 2: Characterization of Ultrafine C3S (UTCS) Particles Obtained in Example 1a Microscopy The final powder of C3S particles after being ultra-finely grinded according to the process as described in example 1a, has been compared by optical microscopy with magnificence to initial C3S particles (coarsely grinded C3S).

FIG. 1 features the significant decreases of particles size for ultrafine C3S particles.

Particle Size

The size distribution of C3S particles after being ultrafinely grinded according to the process as described in example 1a, has been compared to those of micronized C3S particles, coarsely grinded C3S particles and crushed C3S particles (Table 1).

TABLE 1

| features the $d_{10}$, $d_{50}$ and $d_{90}$ sizes for each kind of C3S particles: | | | |
| --- | --- | --- | --- |
| C3S Sample | $d_{10}$ (µm) | $d_{50}$ (µm) | $d_{90}$ (µm) |
| Crushed | 2.0 | 17.0 | 330 |
| Coarsely grinded | 2.1 | 9.8 | 28.0 |
| Micronized | 0.8 | 3.4 | 7.2 |
| Ultrafine batch 1 | 0.6 | 1.5-2.1 | 1.4-6 |
| Ultrafine batch 2 | 0.534 | 0.85 | 1.75 |
| Ultrafine batch 3 | 0.535 | 0.853 | 1.58 |
| Ultrafine batch 4 | 0.504 | 0.795 | 1.50 |
| Ultrafine batch 5 | 0.534 | 0.85 | 1.75 |
| Ultrafine batch 6 | 0.536 | 0.858 | 1.66 |
| Ultrafine batch 7 | 0.568 | 0.857 | 1.51 |
| Ultrafine batch 8 | 0.626 | 1.03 | 2.02 |
| Ultrafine batch 9 | 0.564 | 0.893 | 1.63 |
| Ultrafine batch 10 | 0.61 | 0.993 | 1.95 |

The results show that the process of the invention strongly decreases the size distribution of the particles. Especially, ultrafine C3S particles have $d_{10}$, $d_{50}$ and $d_{90}$ sizes over than crushed, coarsely grinded and micronized C3S particles.

Specific surface $S_{spé}$.

The specific surface of C3S particles after being ultrafinely grinded according to the process as described in example 1a, has been compared to those of micronized C3S particles and coarsely grinded C3S particles (Table 2). The specific surface has been measured by the BET technique as described above.

TABLE 2

| features the specific surfaces for each kind of C3S particles: | |
| --- | --- |
| C3S Sample | $S_{spé}$. ($m^2/g$) |
| Crushed | 0.5 ± 0.01 |
| Coarsely grinded | 0.78 ± 0.03 |
| Micronized | 1.56 ± 0.03 |
| Ultrafine batch 1 | 5.17-8.72 ± 0.06 |

TABLE 2-continued

| features the specific surfaces for each kind of C3S particles: | |
|---|---|
| C3S Sample | $S_{sp\acute{e}.}$ (m²/g) |
| Ultrafine batch 7 | 10.2 |
| Ultrafine batch 8 | 7.2 |
| Ultrafine batch 9 | 9.1 |
| Ultrafine batch 10 | 6.5 |

The results show that the specific surface of ultrafine C3S particles is higher than those of coarsely grinded and micronized C3S particles.

Part III: Compositions of the Invention

Example 3: Preparation of Dental Compositions with Different Calcium Silicate Particles Sizes Powder phases A according to the invention and comparative powder phases C (i.e. not comprising ultrafine calcium silicate particles), having the compositions presented in Table 3, were prepared by mixing the powder components.

Liquid phases B according to the invention having the compositions presented in Table 4, were prepared by mixing the components with water.

Then, mixed compositions were prepared by mixing a powder phase A with a liquid phase B in a ratio powder phase/liquid phase (w/w) ranging from 1.5 to 6.

TABLE 3

| Powder phases A and comparative powder phases C | | | | | | |
|---|---|---|---|---|---|---|
| | | Amount (% w/w) | | | | |
| Category | Component | C1-3 | A1 | A2 | A3 | |
| Calcium silicate compounds | Ultrafine C3S | | 80.7 | 40.35 | 24.2 | |
| | Micronized C3S | 80.7 | | | | |
| | Coarsely grinded C3S | | | 40.35 | | |
| | Crushed C3S | | | | 56.5 | |
| | Total amount of CS mixture | 80.7 | 80.7 | 80.7 | 80.7 | |
| Setting accelerators | Calcium carbonate | 14 | 14 | 14 | 14 | |
| | Calcium oxide | 0.25 | 0.25 | 0.25 | 0.25 | |
| | Calcium phosphate | | | | | |
| Radiopacifiers | Zirconium oxide | 5 | 5 | 5 | 5 | |
| | Bismuth oxide | | | | | |
| | Cerium oxide | | | | | |
| Pigments | Iron oxides | 0.05 | 0.05 | 0.05 | 0.05 | |

| | | Amount (% w/w) | | | | |
|---|---|---|---|---|---|---|
| Category | Component | C5 | C6 | A4 | A5 | A6 |
| Calcium silicate compounds | Ultrafine C3S | | | 65 | 32.5 | 19.5 |
| | Micronized C3S | 65 | 65 | | | |
| | Coarsely grinded C3S | | | | 32.5 | |
| | Crushed C3S | | | | | 45.5 |
| | Total amount of CS mixture | 65 | 65 | 65 | 65 | 65 |
| Setting accelerators | Calcium carbonate | 14 | 14 | 14 | 14 | 14 |
| | Calcium oxide | | | | | |
| | Calcium phosphate | | | | | |
| Radiopacifiers | Zirconium oxide | 20 | 6 | 16 | 20 | 6 |
| | Bismuth oxide | | 6 | | | 6 |
| | Cerium oxide | | 6 | | | 6 |
| Pigments | Iron oxides | 1 | 3 | 5 | 1 | 3 |

TABLE 3-continued

| Powder phases A and comparative powder phases C | | | | | | |
|---|---|---|---|---|---|---|
| | | Amount (% w/w) | | | | |
| Category | Component | C7 | A7 | A7bis | A8 | A9 |
| Calcium silicate compounds | Ultrafine C3S | | 50 | 50.67 | 27.5 | 17.4 |
| | Micronized C3S | 50 | | | | |
| | Coarsely grinded C3S | | | | 27.5 | |
| | Crushed C3S | | | | | 40.6 |
| | Total amount of CS mixture | 50 | 50 | 50.67 | 55 | 58 |
| Setting accelerators | Calcium carbonate | 14 | 14 | 14 | 10 | 14 |
| | Calcium oxide | 3 | 3 | 0.25 | 3 | 6 |
| | Calcium phosphate | 3 | 3 | | 5 | |
| Radiopacifiers | Zirconium oxide | 5 | 5 | 35 | 5 | 5 |
| | Bismuth oxide | 10 | 10 | | | 7 |
| | Cerium oxide | | | | 8 | 5 |
| Pigments | Iron oxides | 15 | 15 | 0.08 | 14 | 5 |

| | | Amount (% w/w) | | | |
|---|---|---|---|---|---|
| Category | Component | C10 | A10 | A11 | A12 |
| Calcium silicate compounds | Ultrafine C3S | | 91 | 46 | 27.9 |
| | Micronized C3S | 91 | | | |
| | Coarsely grinded C3S | | | 46 | |
| | Crushed C3S | | | | 65.1 |
| | Total amount of CS mixture | 91 | 91 | 92 | 93 |
| Setting accelerators | Calcium carbonate | 9 | 9 | 8 | 7 |
| | Calcium oxide | | | | |
| | Calcium phosphate | | | | |
| Radiopacifiers | Zirconium oxide | | | | |
| | Bismuth oxide | | | | |
| | Cerium oxide | | | | |
| Pigments | Iron oxides | | | | |

| | | Amount (% w/w) | | | |
|---|---|---|---|---|---|
| Category | Component | A13 | A14 | A15 | A16 |
| Calcium silicate compounds | Ultrafine C3S | 40 | 32.5 | 29.5 | 47.5 |
| | Ultrafine C2S | 40 | 32.5 | 29.5 | 47.5 |
| | Micronized C2S | | | | |
| | Total amount of CS mixture | 80 | 65 | 59 | 95 |
| Setting accelerators | Calcium carbonate | 14 | 20 | 14 | |
| | Calcium oxide | 0.25 | | 2 | |
| | Calcium phosphate | | | 3 | |
| Radiopacifiers | Zirconium oxide | 5 | 10 | 5 | |
| | Bismuth oxide | | | 3 | 5 |
| | Cerium oxide | | | 9 | |
| Pigments | Iron oxides | 0.75 | 5 | 5 | |

| | | Amount (% w/w) | | | |
|---|---|---|---|---|---|
| Category | Component | A17 | A18 | A19 | A20 |
| Calcium silicate compounds | Ultrafine C3S | 40 | 32.5 | 29.5 | 47 |
| | Ultrafine C2S | | | | |
| | Micronized C2S | 40 | 32.5 | 29.5 | 47 |
| | Total amount of CS mixture | 80 | 65 | 59 | 94 |
| Setting accelerators | Calcium carbonate | 14 | 9 | 14 | 6 |
| | Calcium oxide | 0.25 | | 5 | |
| | Calcium phosphate | | | 1 | |
| Radiopacifiers | Zirconium oxide | 5 | 25 | 5 | |
| | Bismuth oxide | | | 8 | |
| | Cerium oxide | | | 3 | |
| Pigments | Iron oxides | 0.75 | 1 | 5 | |

TABLE 3-continued

Powder phases A and comparative powder phases C

| | | Amount (% w/w) | | | |
|---|---|---|---|---|---|
| Category | Component | A21 | A22 | A21 | A24 |
| Calcium silicate compounds | Ultrafine C3S | 40 | 32.5 | 25 | 47.5 |
| | Portland cement MTA | 40 | 32.5 | 25 | 47.5 |
| Total amount of CS mixture | | 80 | 65 | 50 | 95 |
| Setting accelerators | Calcium carbonate | 14 | 14 | 14 | |
| | Calcium oxide | 0.25 | | 3 | |
| | Calcium phosphate | | | 3 | |
| Radiopacifiers | Zirconium oxide | 5 | 6 | 5 | |
| | Bismuth oxide | | 6 | 10 | 5 |
| | Cerium oxide | | 6 | | |
| Pigments | Iron oxides | 0.75 | 3 | 15 | |

| | | Amount (% w/w) | | | |
|---|---|---|---|---|---|
| Category | Component | A25 | A26 | A27 | A28 |
| Calcium silicate compounds | Ultrafine C3S | 40 | 32.5 | 25 | 47.5 |
| | Portland cement MTA | 40 | 32.5 | 25 | 47.5 |
| Total amount of CS mixture | | 80 | 65 | 50 | 95 |
| Setting accelerators | Calcium carbonate | 14 | 14 | 14 | |
| | Calcium oxide | 0.25 | | 3 | |
| | Calcium phosphate | | | 3 | |
| Radiopacifiers | Zirconium oxide | 5 | 16 | 5 | |
| | Bismuth oxide | | | 10 | 5 |
| | Cerium oxide | | | | |
| Pigments | Iron oxides | 0.75 | 5 | 15 | |

TABLE 4

Liquid phases B

| | | Amount (% w/w) | | | | | | |
|---|---|---|---|---|---|---|---|---|
| Category | Component | B1 | B1bis | B2 | B3 | B4 | B4bis | B5 |
| Aqueous liquid | Water | 85 | 69 | 42.5 | 37.5 | 60 | 60 | 45.5 |
| Non-aqueous liquids | Ethylene glycol | | | 42.5 | | | | 19.5 |
| | Polyethylene glycol (M = 4000 g/mol) | | | | 37.5 | 15 | | |
| | Polyethylene glycol (M = 300 g/mol) | | | | | | 15 | |
| Total aqueous + non-aqueous liquid | | 85 | 69 | 85 | 75 | 75 | 75 | 65 |
| Setting accelerator | Calcium chloride | 15 | 29 | 10 | 8 | 20 | 20 | |
| Water reducing agents | Glenium | | | 5 | | | | |
| | Polynaphtalenesulfonate | | | | 5 | | | |
| | Modified polycarboxylate | | | 2 | 12 | 5 | 5 | 35 |

Part IV: Properties of the Compositions of the Invention

Example 4: Comparison of the Setting Time of Dental Compositions Comprising Ultrafine C3S Particles with Composition Comprising Non-Ultrafine C3S Particles This experiment aims to evaluate the improvement in terms of setting time of self-hardening dental compositions comprising ultrafine C3S particles, while keeping good handling properties such as appearance and working time, compared to compositions devoid of ultrafine C3S particles but comprising instead micronized C3S particles.

Several compositions according to the invention have been prepared by mixing one of the powder phase A1, A2, A5, A6, A7 or A10 as described in Table 3, with one of the liquid phase B1 bis, B4 or B4 bis as described in Table 4.

For comparison, compositions equivalent to above composition but comprising only micronized C3S particles were prepared by mixing one of the powder phases C1-3, C5, C6, C7 or C10 as described in Table 3, with one of the liquid phase B1 bis, B4 or B4 bis as described in Table 4.

Ratio p/l

First, experiments have been carried out for determining suitable mass ratios of the powder phase to the liquid phase (ratio p/l) for each of the compositions, in order to provide a homogenous creamy appearance when mixing the powder phase with the liquid phase. Especially, various proportions of powder phase and liquid phase were tested until the expected creamy appearance is obtained.

The ratio reported in Table 5 were determined as being suitable to provide expected appearance and workability to the composition.

TABLE 5

| | Mass ratios (powder phase/liquid phase) | | |
|---|---|---|---|
| | B1 bis | B4 | B4 bis |
| C1-3 | 3.4 | ND | ND |
| A1 | 2.7 | ND | ND |

TABLE 5-continued

| | Mass ratios (powder phase/liquid phase) | | |
|---|---|---|---|
| | B1 bis | B4 | B4 bis |
| A2 | 3.9 | ND | ND |
| C5 | 3.4 | 4.6 | 5.1 |
| A5 | 3.3 | 3.7 | 4.1 |
| C6 | 3.4 | 4.6 | 5.3 |

TABLE 5-continued

| | Mass ratios (powder phase/liquid phase) | | |
| --- | --- | --- | --- |
| | B1 bis | B4 | B4 bis |
| A6 | 3.3 | ND | ND |
| C7 | 2.8 | 4.2 | 5.1 |
| A7 | 1.9 | ND | ND |
| C10 | 3.2 | 4.1 | ND |
| A10 | 2.3 | ND | ND |

ND: not determined

Therefore, the adaptation of the ratio p/l enables to provide a suitable texture, and depends on the compositions of the powder and liquid phases used for the mixture.

Setting Time

The setting time of the compositions obtained by mixing powder phases A and liquid phases B in above determined ratios was measured. Results are provided in Table 6 and also represented in FIGS. 2 and 3.

TABLE 6

| | Setting times (min) | | |
| --- | --- | --- | --- |
| | B1 bis | B4 | B4 bis |
| C1-3 | 12.0 | ND | ND |
| A1 | 5.1 | ND | ND |
| A2 | 4.4 | ND | ND |
| C5 | 16.5 | 14.7 | 16.7 |
| A5 | 5.8 | 7.1 | 6.9 |
| C6 | 16.9 | 16.3 | 19.0 |
| A6 | 9.4 | ND | ND |
| C7 | 20.6 | 14.5 | 11.5 |
| A7 | 10.6 | ND | ND |
| C10 | 16.7 | 17.2 | ND |
| A10 | 7.3 | ND | ND |

ND: not determined

Figure 2:
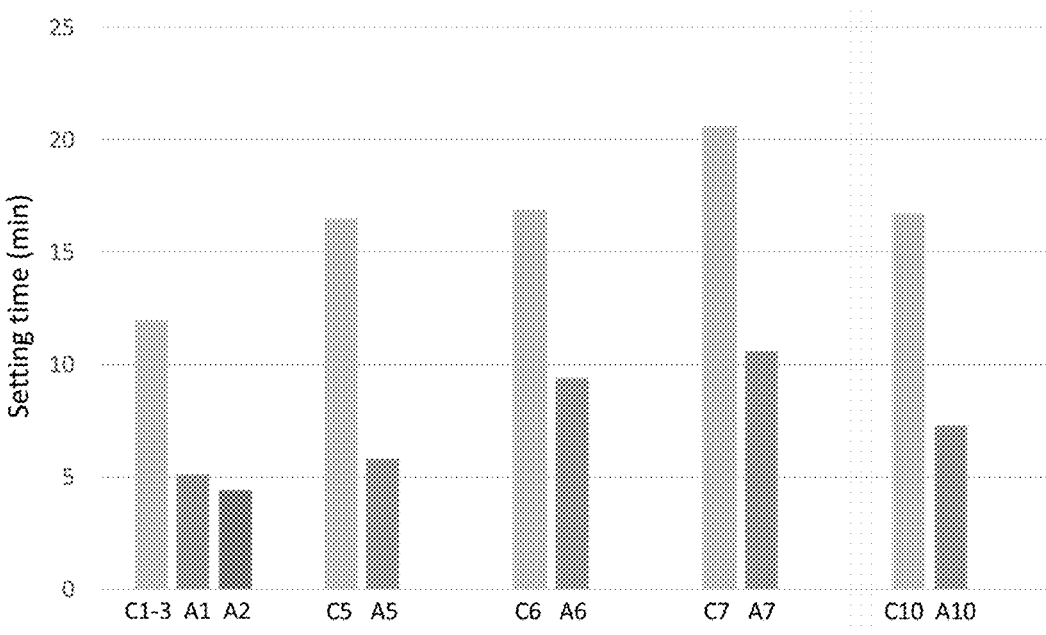
FIG. 2 is a set of histograms showing the setting time for each mixture obtained by mixing one of the powder phases comprising ultrafine C3S particles A1, A2, A5, A6, A7 or A10, or a comparative powder phase comprising micronized C3S particles C1-3, C5, C6, C7 or C10, with liquid phase B1 bis.
Figure 3:
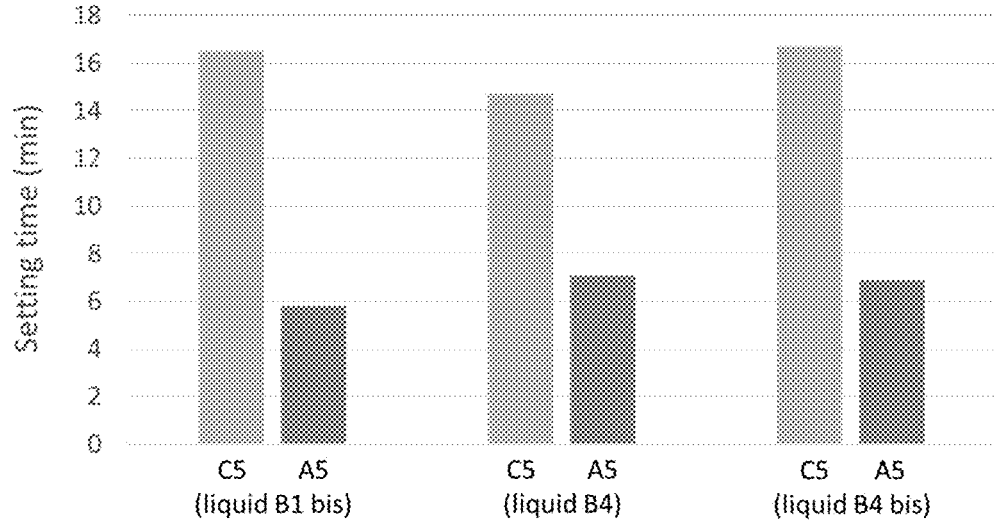
FIG. 3 is a set of histograms showing the setting time for each mixture obtained by mixing the powder phase comprising ultrafine C3S particles A5 or the comparative powder phase comprising micronized C3S particles C5, with liquid phases B1 bis, B4 or B4 bis.

As evidence with above results and as clearly represented in FIGS. 2 and 3, the use of the ultrafine calcium silicate particles of the invention enable to significantly reduce the setting time of the compositions, compared to the use of micronized calcium silicate particles only.

Especially, it is shown in FIG. 2 that the use of the liquid phase B1 bis with the various powder phases of the invention (A1, A2, A5, A6, A7 and A10) compared with their equivalent phases comprising only micronized calcium silicate particles (C1-3, C5, C6, C7, and C10) enables to reduce the setting time by at least 44% (A6 vs C6) up to 65% (A5 vs C5), with a mean of about 56% for these compositions.

In FIG. 3, it is evidenced that whatever the liquid phase that is used (B1 bis, B4 or B4bis), the reduction of the setting time can be obtained by using a powder phase of the invention (A5) compared with the equivalent phase comprising only micronized calcium silicate particles (C5).

Compressive Strength

Example 5: Comparison of the Compressive Strength of Dental Compositions Comprising Ultrafine C3S Particles with Composition Comprising Non-Ultrafine C3S Particles This experiment aims to evaluate the retention of compressive of self-hardening dental compositions comprising ultrafine C3S particles, compared to compositions devoid of ultrafine C3S particles but comprising instead micronized C3S particles.

Several compositions were prepared by mixing powder phase A2 or A7bis as described in Table 3, with liquid phase B1 bis as described in Table 4. Powder phase C1-3 comprising micronized C3S particles instead of ultrafine C3S particles was used for comparison.

Different batches of C3S particles were used for the ultrafine C3S particles. The size distributions of the C3S particles used in the compositions of this example are detailed in Table 7.

TABLE 7

| $d_{10}$, $d_{50}$ and $d_{90}$ sizes for the batches of C3S particles used in this example: | | | |
| --- | --- | --- | --- |
| C3S Sample | $d_{10}$ (μm) | $d_{50}$ (μm) | $d_{90}$ (μm) |
| Coarsely grinded | 2.4 | 9.3 | 25 |
| Micronized | 0.8 | 3.4 | 7.2 |
| Ultrafine U1 | 0.5 | 1.04 | 2.05 |
| Ultrafine U2 | 0.72 | 1.29 | 2.47 |
| Ultrafine U3 | 0.76 | 1.50 | 3.12 |
| Ultrafine U4 | 0.82 | 1.93 | 4.55 |

Figure 4:
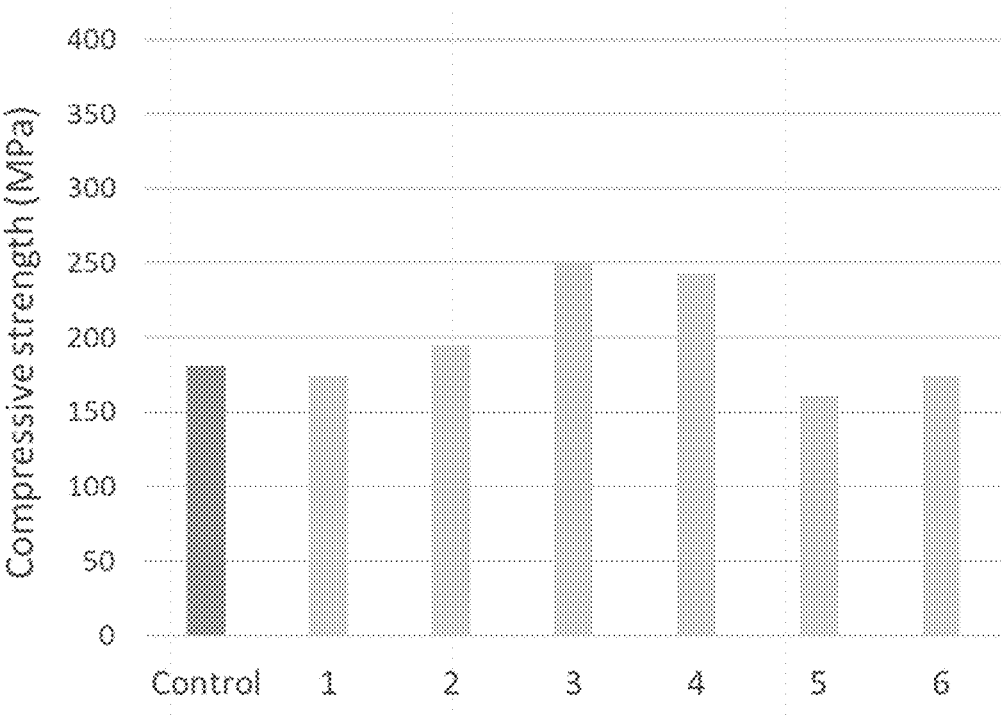
FIG. 4 is a set of histograms showing the compressive strength for each hardened material obtained in example 6.

The compressive strength of the hardened material was measured and results are reported in Table 8 and also represented in FIG. 4.

TABLE 8

| Compositions, weight ratio powder/liquid and compressive strength: | | | | | | | |
| --- | --- | --- | --- | --- | --- | --- | --- |
| Assay number | Control | 1 | 2 | 3 | 4 | 5 | 6 |
| Powder phase A | C1-3 | A2 | A2 | A2 | A2 | A7bis | A7bis |
| Liquid phase B | B1Bis | B1Bis | B1Bis | B1Bis | B1Bis | B1Bis | B1Bis |
| Ratio powder/liquid | 3.04 | 3.33 | 3.79 | 4.19 | 4.19 | 3.56 | 3.91 |
| Ultrafine C3S batch | \ | U1 | U2 | U3 | U4 | U3 | U4 |
| Compressive strength (Mpa) | 181.1 | 173.9 | 194.3 | 250.2 | 243.2 | 160.9 | 174.5 |

As evidence with above results and as clearly represented in FIG. 4, the use of the ultrafine calcium silicate particles of the invention enable to maintain or even increase the compressive strength of the hardened restorative material, compared to the materials obtained using micronized calcium silicate particles.

The invention claimed is:

1. A kit for producing a dental restoration material, said kit comprising:
   a first container containing a powder phase comprising:
      from 15% to 98% in weight of the total weight of the powder phase of ultrafine particles of calcium silicate having a $d_{10}$ size ranging from 0.4 µm to 0.8 µm, a $d_{50}$ size ranging from 0.7 µm to 2.9 µm and a $d_{90}$ size ranging from 1.3 um to 7 µm, wherein the $d_{10}$, $d_{50}$ and $d_{90}$ sizes are measured by laser diffraction;

from 2% to 35% in weight of the total weight of the powder phase of a radiopacifier; and optionally one or more additive selected from setting accelerators, pigments, water reducing agents, texturing agents, pH stabilizing agents, surfactants, and fillers; and a second container containing an aqueous liquid phase; and wherein the weight ratio of the powder phase present in the kit to the liquid phase present in the kit ranges from 2 to 5.

2. The kit according to claim 1, wherein the calcium silicate is selected from tricalcium silicate (C3S), dicalcium silicate (C2S) and any combinations thereof.

3. The kit according to claim 1, wherein the powder phase comprises a Portland cement and/or mineral trioxide aggregates (MTA), as ultrafine calcium silicate particles.

4. The kit according to claim 1, wherein the powder phase further comprises non-ultrafine particles of calcium silicate.

5. The kit according to claim 1, wherein the amount of ultrafine calcium silicate particles ranges from 10% to 100% by weight to the total weight of calcium silicate present in the powder phase.

6. The kit according to claim 1, wherein the radiopacifier is selected from zirconium oxide, bismuth oxide, cerium oxide, barium sulphate, calcium tungstate, titanate dioxide, ytterbium oxide and mixtures thereof.

7. The kit according to claim 1, wherein the powder phase comprises one or more additive, wherein the additive is selected from setting accelerators; and pigments.

8. The kit according to claim 1, wherein the powder phase comprises:

from 20% to 60% in weight of the total weight of the powder phase of ultrafine particles of tricalcium silicate having:

a specific area, measured by BET technique, ranging from 3 to 11 m²/g;

a $d_{10}$ size ranging from 0.4 µm to 0.8 µm;

a $d_{50}$ size ranging from 0.7 µm to 2.9 µm; and a $d_{90}$ size ranging from 1.3 µm to 7 µm;

wherein the $d_{10}$, $d_{50}$ and $d_{90}$ sizes are measured by laser diffraction;

from 0% to 50% in weight of the total weight of the powder phase of non-ultrafine particles of calcium silicate;

from 2% to 35% in weight of the total weight of the powder phase of a radiopacifier; and from 0% to 25% in weight of the total weight of the powder phase of one or more setting accelerator.

9. The kit according to claim 1, wherein the aqueous liquid phase consists of water.

10. The kit according to claim 1, wherein the aqueous liquid phase comprises water and one or more additive, wherein the additive is selected from setting accelerators and water reducing agents.

11. The kit according to claim 10, wherein the aqueous liquid phase comprises:

from 60% to 85% in weight of the total weight of the aqueous liquid phase of water;

from 5% to 35% in weight of the total weight of the aqueous liquid phase of setting accelerator; and from 0% to 5% in weight of the total weight of the aqueous liquid phase of water reducing agent.

12. A dental composition obtained by mixing the whole content of the first container with the whole content of the second container of the kit according to claim 1.

13. A medical device comprising the kit according to claim 1.

14. The medical device according to claim 13, wherein the medical device is an injection system.

15. The kit according to claim 5, wherein the amount of ultrafine calcium silicate particles ranges from 10% to 70% by weight to the total weight of calcium silicate present in the powder phase.

16. The kit according to claim 7, wherein the setting accelerator is selected from calcium carbonate, calcium oxide, calcium phosphate and mixture thereof.

17. The kit according to claim 7, wherein the pigment is an iron oxide.

18. The kit according to claim 11, wherein the setting accelerator is calcium chloride.

19. The kit according to claim 11, wherein the water reducing agent is a modified polycarboxylate.

20. The medical device according to claim 14, wherein the medical device is a syringe.

* * * * *